(12) United States Patent
Cai et al.

(10) Patent No.: US 8,710,219 B2
(45) Date of Patent: Apr. 29, 2014

(54) PHOSPHOINOSITIDE 3-KINASE INHIBITOR WITH A ZINC BINDING MOIETY

(75) Inventors: Xiong Cai, Bedford, MA (US); Haixiao Zhai, Bedford, MA (US); Chengjung Lai, Belmont, MA (US); Changgeng Qian, Wayland, MA (US); Rudi Bao, Wellesley, MA (US)

(73) Assignee: Curis, Inc., Lexington, MA (US)

( * ) Notice: Subject to any disclaimer, the term of this patent is extended or adjusted under 35 U.S.C. 154(b) by 10 days.

(21) Appl. No.: 13/435,062

(22) Filed: Mar. 30, 2012

(65) Prior Publication Data

US 2013/0090335 A1    Apr. 11, 2013

Related U.S. Application Data

(60) Provisional application No. 61/559,489, filed on Nov. 14, 2011, provisional application No. 61/470,849, filed on Apr. 1, 2011.

(51) Int. Cl.
*C07D 413/14* (2006.01)
*A61K 31/535* (2006.01)

(52) U.S. Cl.
USPC ........................................ 544/117; 514/234.2

(58) Field of Classification Search
None
See application file for complete search history.

(56) References Cited

U.S. PATENT DOCUMENTS

| | | | |
|---|---|---|---|
| 5,502,187 A | 3/1996 | Ayer et al. | |
| 6,087,367 A | 7/2000 | Breslow et al. | |
| 6,608,053 B2 | 8/2003 | Hayakawa et al. | |
| 6,777,217 B1 | 8/2004 | Schreiber et al. | |
| 7,300,935 B2 | 11/2007 | Cho et al. | |
| 7,846,929 B2 | 12/2010 | Folkes et al. | |
| 7,888,352 B2 | 2/2011 | Bayliss et al. | |
| 8,367,663 B2 * | 2/2013 | Cai et al. | 514/234.2 |
| 8,461,157 B2 * | 6/2013 | Cai et al. | 514/234.2 |
| 2007/0249587 A1 | 10/2007 | Yonetoku et al. | |
| 2008/0076768 A1 | 3/2008 | Chuckowree et al. | |
| 2008/0076774 A1 | 3/2008 | Anand et al. | |
| 2008/0125440 A1 | 5/2008 | Cai et al. | |
| 2008/0125478 A1 | 5/2008 | Cai et al. | |
| 2008/0139590 A1 | 6/2008 | Qian et al. | |
| 2008/0161320 A1 | 7/2008 | Cai et al. | |
| 2008/0194578 A1 | 8/2008 | Qian et al. | |
| 2008/0221132 A1 | 9/2008 | Cai et al. | |
| 2008/0234332 A1 | 9/2008 | Cai et al. | |
| 2008/0242665 A1 | 10/2008 | Bayliss et al. | |
| 2008/0269210 A1 | 10/2008 | Castanedo et al. | |
| 2009/0076044 A1 | 3/2009 | Qian et al. | |
| 2009/0093507 A1 | 4/2009 | Qian et al. | |
| 2010/0222343 A1* | 9/2010 | Cai et al. | 514/234.2 |
| 2010/0233164 A1 | 9/2010 | Ebens, Jr. et al. | |
| 2010/0292468 A1 | 11/2010 | Babu et al. | |
| 2011/0086837 A1 | 4/2011 | Belvin et al. | |
| 2012/0088764 A1 | 4/2012 | Cai et al. | |
| 2013/0102595 A1 | 4/2013 | Bao et al. | |

FOREIGN PATENT DOCUMENTS

| | | |
|---|---|---|
| EP | 1 277 738 A1 | 1/2003 |
| WO | 03075929 A1 | 9/2003 |
| WO | 03076395 A1 | 9/2003 |
| WO | 03076400 A1 | 9/2003 |
| WO | 03076401 A1 | 9/2003 |
| WO | 03076421 A1 | 9/2003 |
| WO | 03076422 A1 | 9/2003 |
| WO | 2004017950 A2 | 3/2004 |
| WO | 2005/097747 A1 | 10/2005 |
| WO | 2006046031 A1 | 5/2006 |
| WO | 2006046035 A1 | 5/2006 |
| WO | 2006046040 A1 | 5/2006 |
| WO | 2006082428 A2 | 8/2006 |
| WO | 2006122926 A1 | 11/2006 |
| WO | 2007082873 A1 | 7/2007 |
| WO | 2007082874 A1 | 7/2007 |
| WO | 2007082880 A1 | 7/2007 |

(Continued)

OTHER PUBLICATIONS

Wozniak, M. B., et al., "Vorinostat interferes with the signaling transduction pathway of T-cell receptor and synergizes with phosphoinositide-3 kinase inhibitors in cutaneous T-cell lymphoma," Haematologica, 95(4): 613-621 (2010).

Ozaki, K.-I., et al., "Blockade of the ERK or PI3K-Akt signaling pathway enhances the cytotoxicity of histone deacetylase inhibitors in tumor cells resistant to gefitinib or imatinib," Biochemical and biophysical research communications, 391(4): 1610-1615 (2010).

Chaussade, C. et al., "Evidence for functional redundancy of class IA PI3K isoforms in insulin signalling," Biochem. J., 404: 449-458 (2007).

(Continued)

*Primary Examiner* — Nyeemah A Grazier
(74) *Attorney, Agent, or Firm* — Elmore Patent Law Group, P.C.; Edgar W. Harlan; Carolyn S. Elmore, Esq.

(57) ABSTRACT

The invention provides a compound of Formula I, (I)

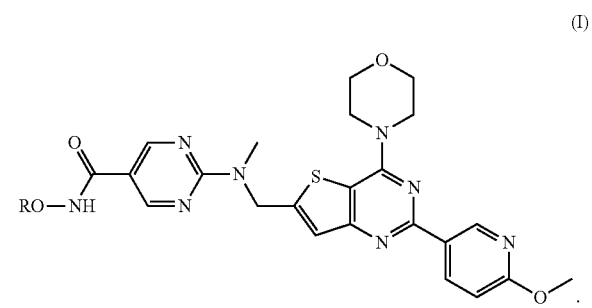

Pharmaceutical compositions comprising such compounds and the use of such compounds in the treatment of phosphoinositide 3-kinase related diseases and disorders such as cancer. The instant application further relates to the treatment of histone deacetylase related disorders and diseases related to both histone deacetylase and phosphoinositide 3-kinase.

8 Claims, 18 Drawing Sheets

(56) References Cited

FOREIGN PATENT DOCUMENTS

| WO | 2007/127175 A2 | 11/2007 |
|---|---|---|
| WO | 2007/129161 A2 | 11/2007 |
| WO | 2007127183 A1 | 11/2007 |
| WO | 2007131364 A1 | 11/2007 |
| WO | 2008/033747 A2 | 3/2008 |
| WO | 2008055068 A2 | 5/2008 |
| WO | 2008070740 A1 | 6/2008 |
| WO | 2008073785 A2 | 6/2008 |
| WO | 2008/100985 A2 | 8/2008 |
| WO | 2009036020 A1 | 3/2009 |
| WO | 2009036057 A1 | 3/2009 |
| WO | 2009036066 A1 | 3/2009 |
| WO | 2009036082 A2 | 3/2009 |
| WO | 2009/055730 A1 | 4/2009 |
| WO | 2009042646 A1 | 4/2009 |
| WO | 2009058895 A1 | 5/2009 |
| WO | 2009086012 A1 | 7/2009 |
| WO | 2009155659 A1 | 12/2009 |
| WO | 2010008847 A2 | 1/2010 |
| WO | 2010/105008 A2 | 9/2010 |
| WO | 2011/054620 A1 | 5/2011 |
| WO | 2011130628 A1 | 10/2011 |

OTHER PUBLICATIONS

Fan, Q.-W., et al., "A Dual Phosphoinositide-3-Kinase α/mTOR Inhibitor Cooperates with Blockade of Epidermal Growth Factor Receptor in PTEN-Mutant Glioma," Cancer Res., 67(17): 7960-7965 (2007).

Hayakawa, M., et al., "Synthesis and biological evaluation of imidazo[1,2-a]pyridine derivatives as novel PI3 kinase p110α inhibitors," Bioorganic & Medicinal Chemistry, 15: 403-412 (2007).

Hayakawa, M., et al., "Synthesis and biological evaluation of 4-morpholino-2-phenylquinazolines and related derivatives as novel PI3 kinase p110α inhibitors," Bioorganic & Medicinal Chemistry, 14: 6847-6858 (2006).

Wegener, D., et al., "Identification of novel small-molecule histone deacetylase inhibitors by medium-throughput screening using a fluorigenic assay," Biochem. Journal, 413: 143-150 (2008).

Yaguchi, S.-I., et al., "Antitumor Activity of ZSTK474, a New Phosphatidylinositol 3-Kinase Inhibitor," Journal of the National Cancer Institute, 98(8): 545-556 (2006).

Engelman, J. A., "Targeting PI3K signalling in cancer: opportunities, challenges and limitations," Nature Reviews Cancer, 9:550-562 (2009).

Curis News Release. Curis Presents Preclinical Data for CU-903 at Keystone Symposia Event, "PI3 Kinase Signaling in Disease." Drugs.com, 2009, pp. 1-2; p. 1 http://www.drugs.comlclinical_trialslcuris-presents-preclinical-data-cu-903-keystone-symposiaevent-8220-pi3-kinase-signaling-8221-7094. html#O_undefined,O_.

Suzuki, T., et. al., "Novel Histone Deacetylase Inhibitors: Design, Synthesis, Enzyme Inhibition, and Binding Mode Study of SAHA-Based Non-hydroxamates," Bioorganic & Medicinal Chemistry Letters, 13: 4321-4326 (2003).

Kulp, S. K., et. al., "Antitumor Effects of a Novel Phenylbutyrate-Based Histone Deacetylase Inhibitor, (S)-HDAC-42, in Prostate Cancer," Clinical Cancer Research, 12(17): 5199-5206 (2006).

Curtin, M., et. al., "Histone Deacetylase Inhibitors: The Abbott Experience," Current Medicinal Chemistry, 10: 2373-2392 (2003).

Minucci, S., et. al., "Histone deacetylase inhibitors and the promise of epigenetic (and more) treatments for cancer," Nature, 6: 38-51 (2006).

Butler, Lisa M., et al., "Suberoylanilide Hydroxamic Acid, an Inhibitor of Histone Deacetylase, Suppresses the Growth of Prostate Cancer Cells in Vitro and in Vivo," Cancer Research, 60: 5165-5170 (2000).

Fan, Qi-Wen, et al., "A dual PI3 kinase/mTOR inhibitor reveals emergent efficacy in glioma," Cancer Cell, 9: 341-349 (2006).

Belvin, Marcia, et al., "PI3K inhibition rescues resistance to EGFR inhibitors in K-Ras mutant and ErbB3 expressing NSCLC cells," Poster number 4004, AACR Apr. 2008, Poster Section 29, Board 2.

Mayo, M. W., et al., "Ineffectiveness of Histone Deacetylase Inhibitors to Induce Apoptosis Involves the Transcriptional Activation of NF-κB through the Akt Pathway," The Journal of Biological Chemistry, 278(21): 18980-18989 (2003).

* cited by examiner

PHOSPHOINOSITIDE 3-KINASE INHIBITOR WITH A ZINC BINDING MOIETY

RELATED APPLICATIONS

This application claims the benefit of U.S. Provisional Application No. 61/470,849, filed on Apr. 1, 2011 and 61/559,489, filed on Nov. 14, 2011. The entire teachings of the above applications are incorporated herein by reference.

BACKGROUND OF THE INVENTION

Phosphoinositides (PIs), which are phosphorylated derivatives of phosphatidylinositol, are essential in eukaryotic cells, regulating nuclear processes, cytoskeletal dynamics, signalling and membrane trafficking. Among the enzymes involved in PI metabolism, PI3-kinases (PI3K) have attracted special attention because of their oncogenic properties and potential as drug targets. PI3-kinases phosphorylate phosphatidylinositols or PIs at the 3-position of the inositol ring. (Lindmo et al. *Journal of Cell Science* 119, 605-614, 2006). The 3-phosphorylated phospholipids generated by PI3K activity bind to the pleckstrin homology (PH) domain of protein kinase B (PKB), causing translocation of PKB to the cell membrane and subsequent phosphorylation of PKB. Phosphorylated PKB inhibits apoptosis-inducing proteins such as FKHR, Bad, and caspases, and is thought to play an important role in cancer progression. The PI3Ks are divided into classes I-III, and class I is further subclassified into classes Ia and Ib. Among these isoforms, class Ia enzymes are thought to play the most important role in cell proliferation in response to growth factor-tyrosine kinase pathway activation (Hayakawa et al., *Bioorganic & Medicinal Chemistry* 14 6847-6858, 2006). Three frequent mutations in cancer constitutively activate PI3Kα and, when expressed in cells, they drive the oncogenic transformation and chronic activation of downstream signalling by molecules such as PKB, S6K and 4E bp1 that is commonly seen in cancer cells. (Stephens et al., *Current Opinion in Pharmacology*, 5(4) 357-365, 2005). As such, PI3-kinases are attractive targets for the treatment of proliferative diseases.

There are several known PI3-kinase inhibitors including Wortmannin and LY294002. Although Wortmannin is a potent PI3K inhibitor with a low nanomolar $IC_{50}$ value, it has low in vivo anti-tumor activity. (Hayakawa et al., *Bioorg. Med. Chem.* 14(20), 6847-6858 (2006)). Recently, a group of morpholine substituted quinazoline, pyridopyrimidine and thienopyrimidine compounds have been reported to be effective in inhibiting PI3kinase p110α. (Hayakawa, 6847-6858). Oral dosage of a morpholine substituted thienopyrimidine compound (GDC-0941) has shown tumor suppression in glioblastoma xenografts in vivo. (Folkes et al., *Journal of Medicinal Chemistry*, 51, 5522-5532, 2008). The following publications disclose a series of thienopyrimidine, pyridopyrimidine and quinazoline based PI3-Kinase inhibitors: WO 2008/073785; WO 2008/070740; WO 2007/127183; U.S. Patent Publication 20080242665.

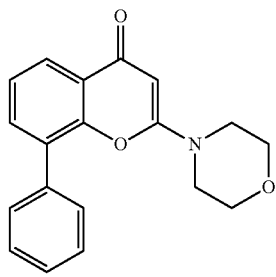

LY294002

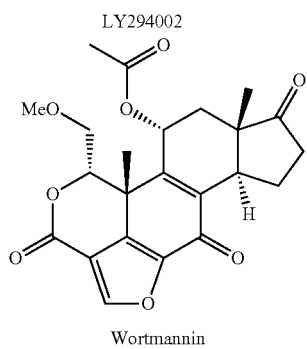

Wortmannin

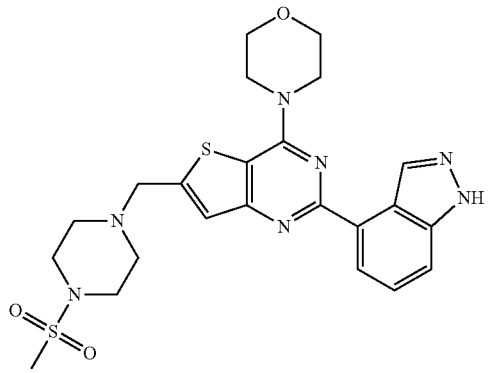

GDC-0941

Histone acetylation is a reversible modification, with deacetylation being catalyzed by a family of enzymes termed histone deacetylases (HDACs). HDAC's are represented by 18 genes in humans and are divided into four distinct classes (*J Mol Biol*, 2004, 338:1, 17-31). In mammalians class I HDAC's (HDAC1-3, and HDAC8) are related to yeast RPD3 HDAC, class 2 (HDAC4-7, HDAC9 and HDAC10) related to yeast HDA1, class 4 (HDAC11), and class 3 (a distinct class encompassing the sirtuins which are related to yeast Sir2).

Csordas, *Biochem. J.*, 1990, 286: 23-38 teaches that histones are subject to post-translational acetylation of the 8-amino groups of N-terminal lysine residues, a reaction that is catalyzed by histone acetyl transferase (HAT1). Acetylation neutralizes the positive charge of the lysine side chain, and is thought to impact chromatin structure. Indeed, access of transcription factors to chromatin templates is enhanced by histone hyperacetylation, and enrichment in underacetylated histone H4 has been found in transcriptionally silent regions of the genome (Taunton et al., *Science*, 1996, 272:408-411). In the case of tumor suppressor genes, transcriptional silencing due to histone modification can lead to oncogenic transformation and cancer.

Several classes of HDAC inhibitors currently are being evaluated by clinical investigators. Examples include hydroxamic acid derivatives, Suberoylanilide hydroxamic acid (SAHA), PXD101 and LAQ824, are currently in the clinical development. In the benzamide class of HDAC inhibitors, MS-275, MGCD0103 and CI-994 have reached clinical trials. Mourne et al. (Abstract #4725, AACR 2005), demonstrate that thiophenyl modification of benzamides significantly enhance HDAC inhibitory activity against HDAC1.

Certain cancers have been effectively treated with such a combinatorial approach; however, treatment regimes using a cocktail of cytotoxic drugs often are limited by dose limiting toxicities and drug-drug interactions. More recent advances with molecularly targeted drugs have provided new approaches to combination treatment for cancer, allowing multiple targeted agents to be used simultaneously, or combining these new therapies with standard chemotherapeutics or radiation to improve outcome without reaching dose limiting toxicities. However, the ability to use such combinations currently is limited to drugs that show compatible pharmacologic and pharmacodynamic properties. In addition, the regulatory requirements to demonstrate safety and efficacy of combination therapies can be more costly and lengthy than corresponding single agent trials. Once approved, combination strategies may also be associated with increased costs to patients, as well as decreased patient compliance owing to the more intricate dosing paradigms required.

SUMMARY OF THE INVENTION

The present invention relates to a compound of Formula I:

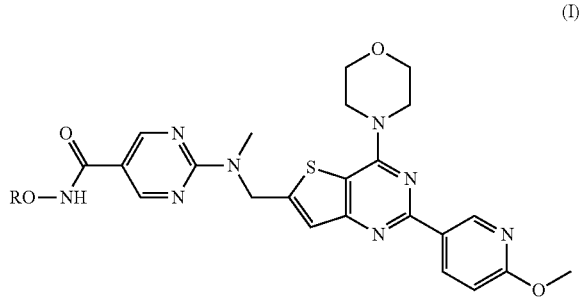

(I)

and pharmaceutically acceptable salts thereof, where R is hydrogen or an acyl group. The acyl group is preferably $R_1C(O)-$, where $R_1$ is substituted or unsubstituted $C_1$-$C_{24}$-alkyl, preferably $C_1$-$C_{10}$-alkyl, and more preferably $C_1$-$C_6$-alkyl; substituted or unsubstituted $C_2$-$C_{24}$-alkenyl, preferably $C_2$-$C_{10}$-alkenyl, and more preferably $C_2$-$C_6$-alkenyl; substituted or unsubstituted $C_2$-$C_{24}$-alkynyl, preferably $C_2$-$C_{10}$-alkynyl, and more preferably $C_2$-$C_6$-alkynyl; substituted or unsubstituted aryl, preferably substituted or unsubstituted phenyl; or substituted or unsubstituted heteroaryl.

The invention also relates to pharmaceutical compositions comprising a compound of Formula I, or a pharmaceutically acceptable salt thereof, in combination with a pharmaceutically acceptable excipient or carrier.

The compounds of Formula I and, in particular, Compound 1, have advantageous properties for use as therapeutic agents, such as for the treatment of cancers and other diseases and disorders associated with PI3 kinase activity and/or HDAC activity. Compound 1, for example, has potent inhibitory activity against the molecular targets PI3K and HDAC and potent antiproliferative activity against a variety of cancer cell lines in vitro. Compound 1 has significant oral bioavailability as observed in animal models. Upon either oral or intravenous dosing in xenograft tumor bearing mice, the compound shows significant uptake by the tumor tissue and pharmacodynamic activity in tumor tissue. Compound 1 also shows substantial antitumor activity in mouse xenograft tumor models following either oral or intravenous administration. The compound also has a favorable safety profile, as shown, for example, by genotoxicity testing using the Ames test.

The invention further relates to the use of the compounds of the invention in the treatment of PI3K related diseases and disorders such as cancer. These compounds further act as an HDAC inhibitor by virtue of its ability to bind zinc ions. The compounds are active at multiple therapeutic targets and are effective for treating a variety of diseases. Moreover, in some cases it has been found that these compounds have enhanced activity when compared to the activities of combinations of separate molecules individually having PI3-Kinase inhibitory activity and HDAC inhibitory activity. In other words, the combination of PI3-kinase and HDAC inhibitory activity in a single molecule may provide a synergistic effect as compared to the PI3-kinase and HDAC inhibitors separately.

Moreover, the efficacy of single-agent PI3K pathway inhibitors is limited by the presence of primary/acquired genetic alterations and activation of multiple pro-survival and growth pathways (Engelman (2009) *Nature Reviews Cancer,* 9: 550-562). Inhibition of PI3K by single-agent PI3K pathway inhibitors can actually upregulate signaling of the RAF-MEK-ERK pathway by the release of negative feedback loops. The compounds of the invention, by virtue of their integrated PI3K/HDAC inhibitory activities, provide the potential to overcome the limitations in the treatment of cancers with single-target PI3K inhibitors. The compounds of the invention disrupt cancer networks in in vivo and in vitro experiments, resulting from durable inhibition of the PI3K-AKT-mTOR pathway, the inhibition of the RAF-MEK-ERK pathway, and the downregulation of receptor tyrosine kinase (RTK) protein levels. In addition, the compounds of the invention induce cell cycle arrest and apoptosis resulting from the upregulation of tumor suppressors p53 and p21 in tumor cell lines in vitro. Accordingly, compounds of the invention have the potential to overcome primary and acquired drug resistance and may be more efficacious than mono-treatment with single-agent PI3K pathway inhibitors in clinical applications.

Another aspect of the invention provides methods of inhibiting PI3 kinase activity, by contacting a PI3 kinase with an effective inhibitory amount of a compound of Formula I, or a pharmaceutically acceptable salt thereof.

DETAILED DESCRIPTION OF THE INVENTION

Figure 1:
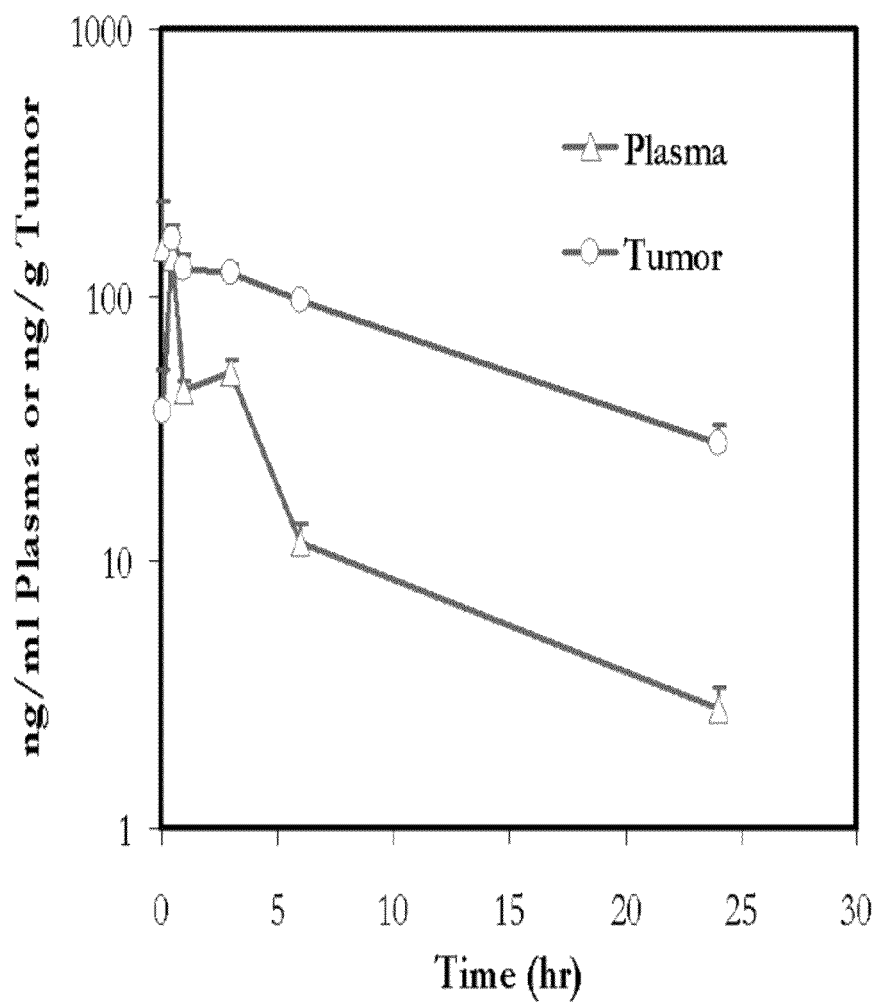
FIG. 1 is a graph of concentration of Compound 1 versus time in plasma and tumor tissue following oral administration to H2122 xenograft tumor-bearing nude mice.

In a preferred embodiment, the compound of Formula I is set forth below:

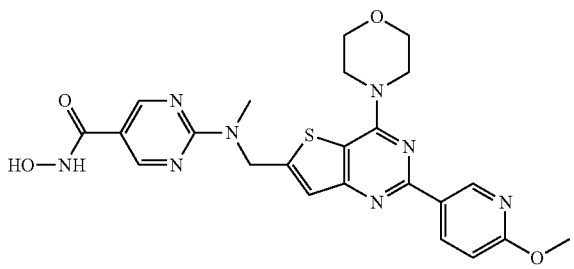 [SMILES: COc1ccc(-c2nc(N3CCOCC3)c3sc(CN(C)c4ncc(C(=O)NO)cn4)cc3n2)cn1]

(hereinafter "Compound 1", also referred to as N-hydroxy-2-(((2-(6-methoxypyridin-3-yl)-4-morpholinothieno[3,2-d]pyrimidin-6-yl)methyl)(methyl)amino)pyrimidine-5-carboxamide or a pharmaceutically acceptable salt thereof.

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In a preferred embodiment, the disease is cancer. In one embodiment, the invention relates to a method of treating cancer in a subject in need of treatment comprising administering to said subject a therapeutically effective amount of a compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the compounds of the invention are used to treat a hematological cancer or hematological precancerous condition. Hematological cancers include leukemias, lymphomas and multiple myeloma. Examples include lymphocytic leukemias, such as acute lymphocytic leukemia, including precursor B acute lymphoblastic leukemia, precursor T acute lymphoblastic leukemia, Burkitt's leukemia, and acute biphenotypic leukemia; and chronic lymphocytic leukemia, including B-cell prolymphocytic leukemia; and myologenous leukemias, such as acute myelogenous leukemia, including acute promyelocytic leukemia, acute myeloblastic leukemia, and acute megakaryoblastic leukemia; and chronic myologenous leukemia, including chronic monocytic leukemia; acute monocytic leukemia. Other leukemias include hairy cell leukemia; T-cell prolymphocytic leukemia; large granular lymphocytic leukemia; and Adult T-cell leukemia. Lymphomas include Hodgkin's lymphoma and Non-Hodgkin's lymphoma, including B-cell lymphomas, T-cell lymphomas, such as cutaneous T-cell lymphoma, and NK cell lymphomas. Hematological precancerous conditions include myelodysplastic syndrome and myeloproliferative disorders, such as primary myelofibrosis, polycythemia vera, and essential thrombocythemia.

Compounds of the invention have been shown to induce reversible lymphopenia and are therefore of use for removing or decreasing the circulating levels of cancer cells of lymphocytic lineage. Such compounds are also of use for treating autoimmune disorders or for modulating an immune response.

In one embodiment, the invention provides a method for reducing the circulating lymphocyte count in a subject, comprising administering to the subject an effective amount of a compound of the invention. In a preferred embodiment, the reduced circulating lymphocyte count is reversible, that is, the circulating lymphocyte count returns to the normal range after dosing with the compound of the invention is stopped. In one embodiment, the reduced circulating lymphocyte count is below the normal range and the subject is lymphopenic. Preferably, the subject derives a therapeutic or prophylactic benefit from the reduced circulating lymphocyte count. Such subjects include those suffering from a hematologic disease, such as a hematologic cancer, those suffering from an autoimmune disorder, and those requiring modulation of an immune response such as patients suffering from diabetes or organ transplant recipients. In a human subject, the circulating lymphocyte count, for example, B-lymphocytes, T-lymphocytes or both, can drop from a normal range to a lymphopenic range. In certain diseases the circulating lymphocyte count is abnormally high. In such diseases, the circulating lymphocyte count can be reduced to the normal range or to a lymphopenic state.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g., HER2/neu, HER3, HER4, ErbB, ErbB2, ErbB3, ErbB4, Xmrk, DER, Let23); fibroblast growth factor (FGF) receptor (e.g., FGF-R1, GFF-R2/BEK/CEK3, FGF-R3/CEK2, FGF-R4/TKF, KGF-R); hepatocyte growth/scatter factor receptor (HGFR) (e.g., MET, RON, SEA, SEX); insulin receptor (e.g. IGFI-R); Eph (e.g., CEK5, CEK8, EBK, ECK, EEK, EHK-1, EHK-2, ELK, EPH, ERK, HEK, MDK2, MDK5, SEK); Axl (e.g., Mer/Nyk, Rse); RET; and platelet-derived growth factor receptor (PDGFR) (e.g., PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g., $p43^{ab1}$, ARG); BTK (e.g., ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g., HSP90), hedgehog pathway-related proteins (e.g., sonic hedgehog, patched, smoothened) and proteosomes.

In a preferred embodiment, subject compounds may be combined with antineoplastic agents (e.g., small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737, GDC-0449, IPI-926, BMS833923, LDE225, PF-04449913 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cyclophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); antimicrotubule agents (Estramustine); retinoids (Bexarotene, Isotretinoin, Tretinoin (ATRA), and Lenalidomide.

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al., (1995) *J. Cancer Res. Clin. Oncol.* 12 1:487). In U.S. Pat. No. 5,484,596, Hanna Jr., et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells.

It will be appreciated that the compounds of the invention may advantageously be used in conjunction with one or more adjunctive therapeutic agents. Examples of suitable agents for adjunctive therapy include a $5HT_1$ agonist, such as a triptan (e.g., sumatriptan or naratriptan); an adenosine A1 agonist; an EP ligand; an NMDA modulator, such as a glycine antagonist; a sodium channel blocker (e.g., lamotrigine); a substance P antagonist (e.g., an $NK_1$ antagonist); a cannabinoid; acetaminophen or phenacetin; a 5-lipoxygenase inhibitor; a leukotriene receptor antagonist; a DMARD (e.g., methotrexate); gabapentin and related compounds; a tricyclic antidepressant (e.g., amitryptilline); a neuron stabilising anti-epileptic drug; a mono-aminergic uptake inhibitor (e.g., venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g., lamivudine) or an immune system modulator (e.g., interferon); an opioid analgesic; a local anaesthetic; a stimulant, including caffeine; an $H_2$-antagonist (e.g., ranitidine); a proton pump inhibitor (e.g., omeprazole); an antacid (e.g. aluminium or magnesium hydroxide); an antiflatulent (e.g., simethicone); a decongestant (e.g., phenylephrine, phenylpropanolamine, pseudoephedrine, oxymetazoline, epinephrine, naphazoline, xylometazoline, propylhexedrine, or levo-desoxyephedrine); an antitussive (e.g., codeine, hydrocodone, carmiphen, carbetapentane, or dextramethorphan); a diuretic; or a sedating or non-sedating antihistamine.

The compounds may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Antiproliferative disorders (e.g., cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including the prevention and treatment of ischemia-related or reperfusion-related vascular and myocardial tissue damage, heart failure, restenosis and arteriosclerosis; Fibrotic diseases including liver fibrosis, cystic fibrosis and angiofibroma; Infectious diseases including Fungal infections, such as candidiasis or *Candida Albicans*, Bacterial infections, Viral infections, such as Herpes Simplex, poliovirus, rhinovirus and coxsackievirus, Protozoal infections, such as Malaria, *Leishmania* infection, *Trypanosoma brucei* infection, Toxoplasmosis and coccidlosis and Haematopoietic disorders including thalassemia, anemia and sickle cell anemia.

The compounds of the invention can also be used in the treatment of a disorder involving, relating to or, associated with dysregulation of PI3 kinase. PI3 kinase activity has been implicated in or shown to be involved in a variety of disorders. In certain cases, PI3 kinase activity is involved in triggering disease onset, while in others, symptoms are known or have been shown to be alleviated by inhibitors of PI3 kinase activity. Disorders of this type that would be expected to be amenable to treatment with the compounds of the invention include but are not limited to cancers, including leukemia, skin cancer, bladder cancer, breast cancer, uterine cancer, ovarian cancer, prostate cancer, lung cancer, colon cancer, pancreatic cancer, renal cancer, gastric cancer and brain cancer; restenosis, atherosclerosis, bone disorders, arthritis, diabetic retinopathy, psoriasis, benign prostatic hypertrophy, atherosclerosis, inflammation, angiogenesis, immunological disorders, pancreatitis and kidney disease.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with aberrations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpes virus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as: A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration; and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII. Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. The invention also encompasses solvates of the compounds of the invention and pharmaceutical compositions comprising such solvates, such as hydrates, methanolates or ethanolates. The term "solvate" refers to a solid, preferably crystalline, form of a compound which includes the presence of solvent molecules within the crystal lattice. A solvate of a compound comprising a given solvent is typically prepared by crystallization of the compound from that solvent. Solvates can include a variety of solvents, including water, methanol and ethanol. The term "hydrate" refers to a solvate in which the solvent is water, and includes, but is not limited to, hemihydrate, monohydrate, dihydrate, trihydrate and the like. The invention further encompasses pharmaceutical compositions comprising any solid or liquid physical form of the compound of the invention, including crystalline and crystalline solvate forms. For example, the compounds can be in a crystalline form, in an amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or solvates thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection, etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, polyethylene glycol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Formulations of the invention intended for oral administration can include one or more permeation enhancers, including long chain fatty acids or salts thereof, such as decanoic acid and sodium decanoate.

In one preferred embodiment, the compound can be formulated in an aqueous solution for intravenous injection. In one embodiment, solubilizing agents can be suitably employed. A particularly preferred solubilizing agent includes cyclodextrins and modified cyclodextrins, such as sulfonic acid substituted β-cyclodextrin derivative or salt thereof, including sulfobutyl derivatized-β-cyclodextrin, such as sulfobutylether-7-β-cyclodextrin which is sold by CyDex, Inc. under the tradename CAPTISOL®.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle", "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6-membered, preferably 5 or 6-membered, heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered, preferably 5- or 6-membered, heteromonocyclic group containing an oxygen atom, for example, pyranyl, furyl, etc.; unsaturated 3 to 6-membered heteromonocyclic group containing a sulfur atom, for example, thienyl, etc.; unsaturated 3 to 6-membered, preferably 5- or 6-membered, heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered, preferably 5- or 6-membered, heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms in the heterocyclo radicals.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g., $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta 3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The terms "compound" and "compound of the invention", as used herein, refer to compounds of Formula I and pharmaceutically acceptable salts thereof. The compounds of the invention can be obtained in different forms, including crystalline and amorphous forms. The compounds can also occur as solvates, for example, hydrates, or solvates of an organic solvent, preferably a pharmaceutically acceptable solvent. The compounds can also occur in multiple crystalline, or polymorphic, forms. The compounds of the invention further include pharmaceutically acceptable prodrugs and esters of the compounds of Formula I.

The term "device" refers to any appliance, usually mechanical or electrical, designed to perform a particular function.

As used herein, the term "dysplasia" refers to abnormal cell growth, and typically refers to the earliest form of pre-cancerous lesion recognizable in a biopsy by a pathologist.

As used herein, the term "effective amount of the subject compounds," with respect to the subject method of treatment, refers to an amount of the subject compound which, when delivered as part of desired dose regimen, brings about, e.g., a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "PI3 kinase related disease or disorder" refers to a disease or disorder characterized by inappropriate phosphoinositide-3-kinase activity or over-activity of the phosphoinositide-3-kinase. Inappropriate activity refers to either: (i) PI3 kinase expression in cells which normally do not express PI3 kinase; (ii) increased PI3 kinase expression leading to unwanted cell proliferation, differentiation and/or growth; or, (iii) decreased PI3 kinase expression leading to unwanted reductions in cell proliferation, differentiation and/or growth. Over-activity of PI3 kinase refers to either amplification of the gene encoding a particular PI3 kinase or production of a level of PI3 kinase activity which can correlate with a cell proliferation, differentiation and/or growth disorder (that is, as the level of the PI3 kinase increases, the severity of one or more of the symptoms of the cellular disorder increases).

The phrase a "radio therapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (Teas).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical *Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl sulfonate having from 1 to 6 carbon atoms, sulfonate and aryl sulfonate. Certain salts such as the sodium, potassium and choline base salts as well as acidic salts such as sulfate and methanesulfonate salts have been found to improve the solubility of compounds of Formula I in pharmaceutically acceptable aqueous media. In one embodiment, the pharmaceutically acceptable salt of Compound 1 is the choline salt. Preferred salts of Compound 1 include the sodium salt and the potassium salt. Other preferred salts include the sulfate and methanesulfonate salts.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, Vol. 4, Academic Press (1985); Krogsgaard-Larsen, et al., (ed.), "Design and Application of Prodrugs, Textbook of Drug Design and Development, Chapter 5, 113-191 (1991); Bundgaard, et al., *Journal of Drug Deliver Reviews,* 8:1-38 (1992); Bundgaard, J. of *Pharmaceutical Sciences,* 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: *Chemistry, Biochemistry And Enzymology*, John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art.

Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Pharmaceutical Compositions

The pharmaceutical compositions of the present invention comprise a therapeutically effective amount of a compound of the invention formulated together with one or more pharmaceutically acceptable carriers or excipients.

Preferably, the pharmaceutically acceptable carrier or excipient is a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta- ($\beta$) and gamma- ($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration (e.g., inhalation into the respiratory system). Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The synthesis of Compound 1 and the methanesulfonate, sodium, potassium and choline salts thereof is illustrated in the schemes below.

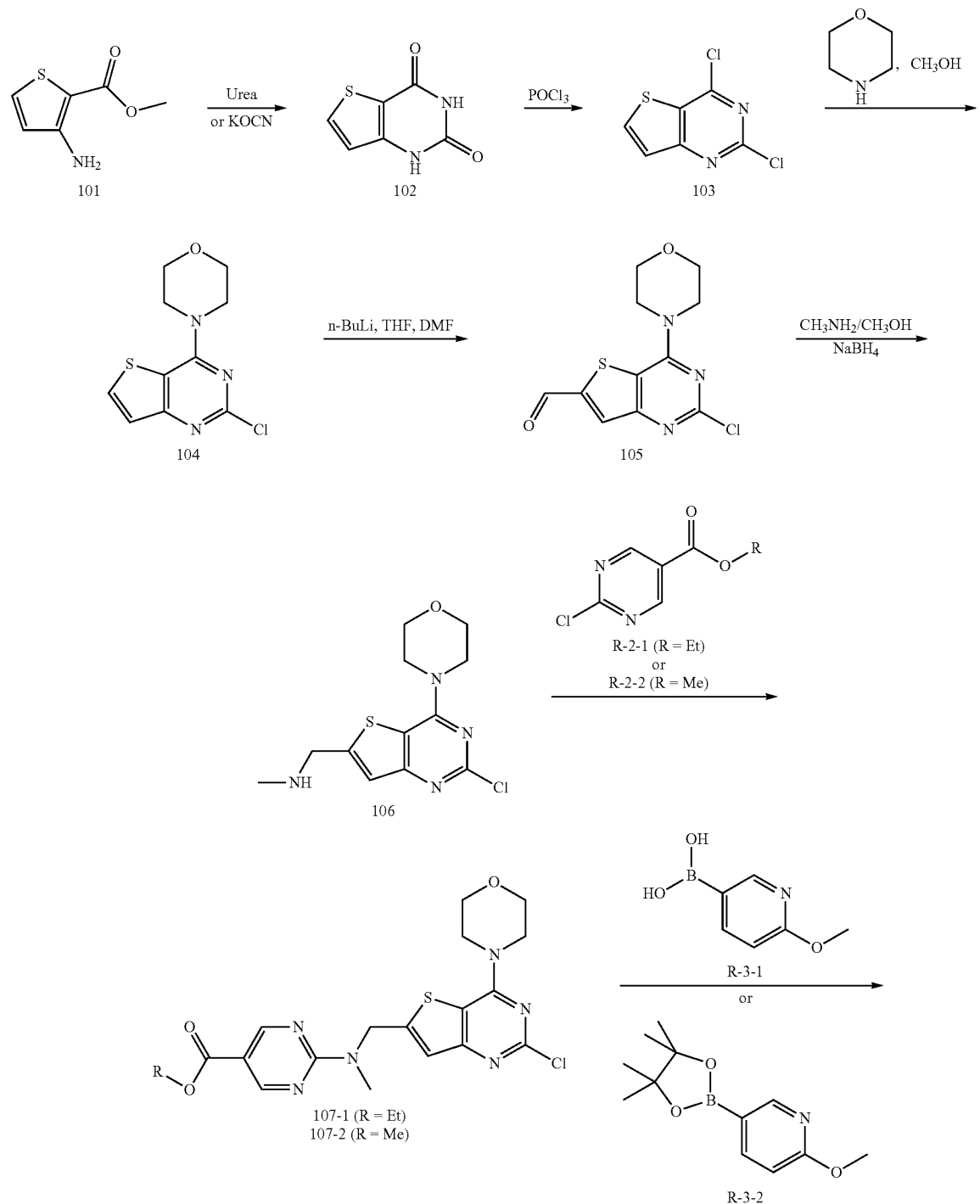

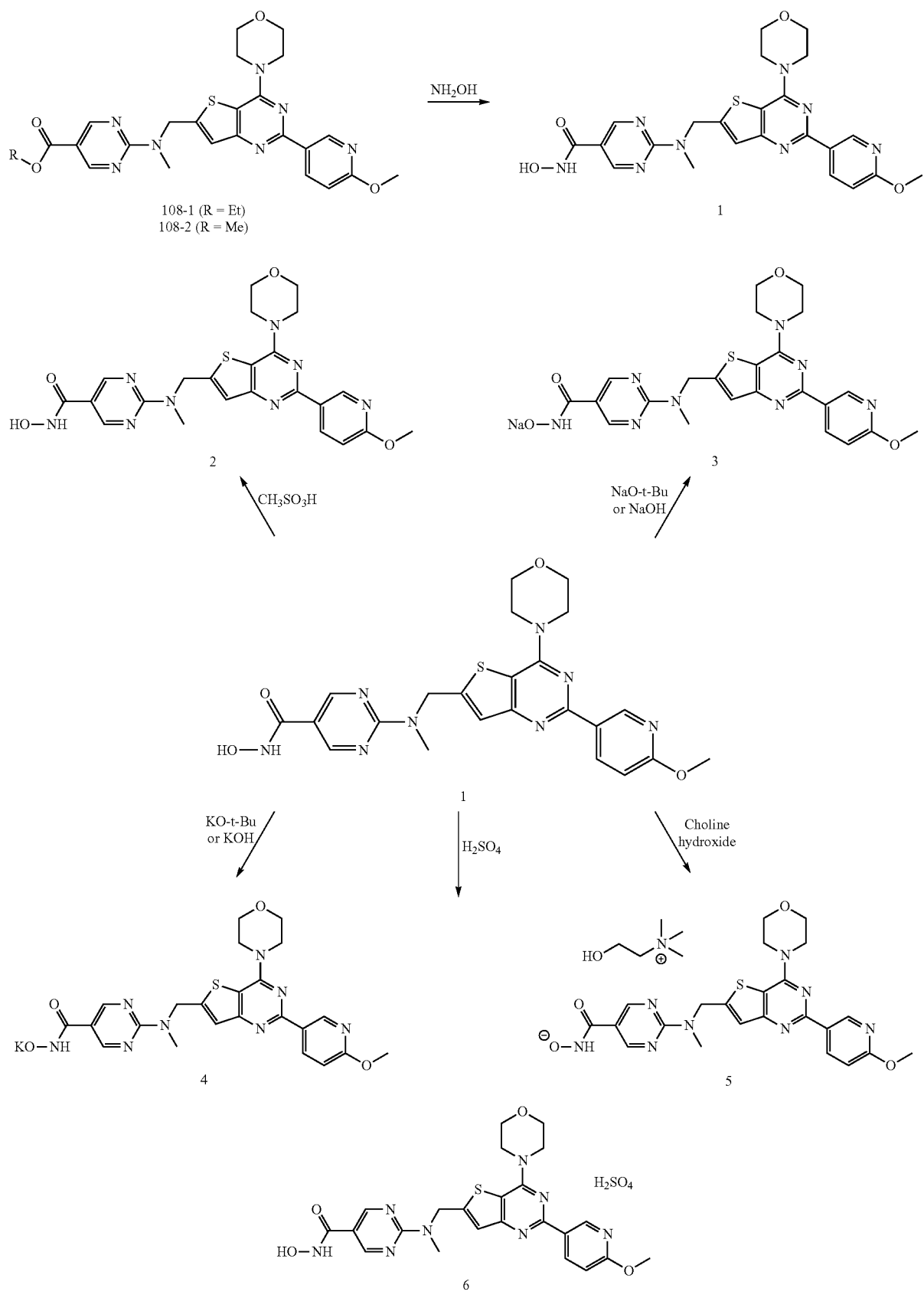

The intermediate 107-1 or 107-2 can be prepared by reacting 106 with either R-2-1 or R-2-2, respectively. The synthetic schemes for the synthesis of R-2-1 and R-2-2 are illustrated below:
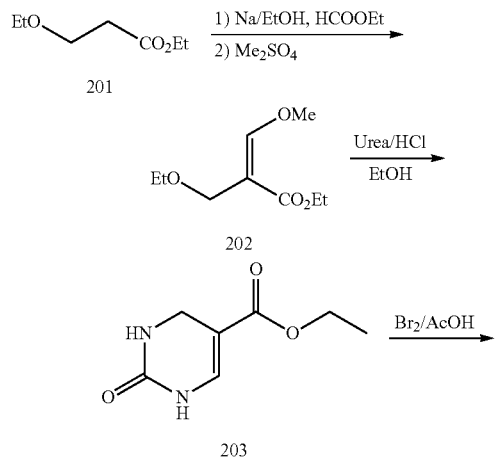
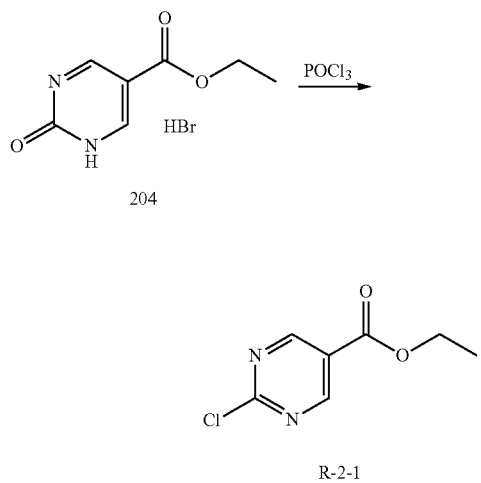
Or by an alternative method:
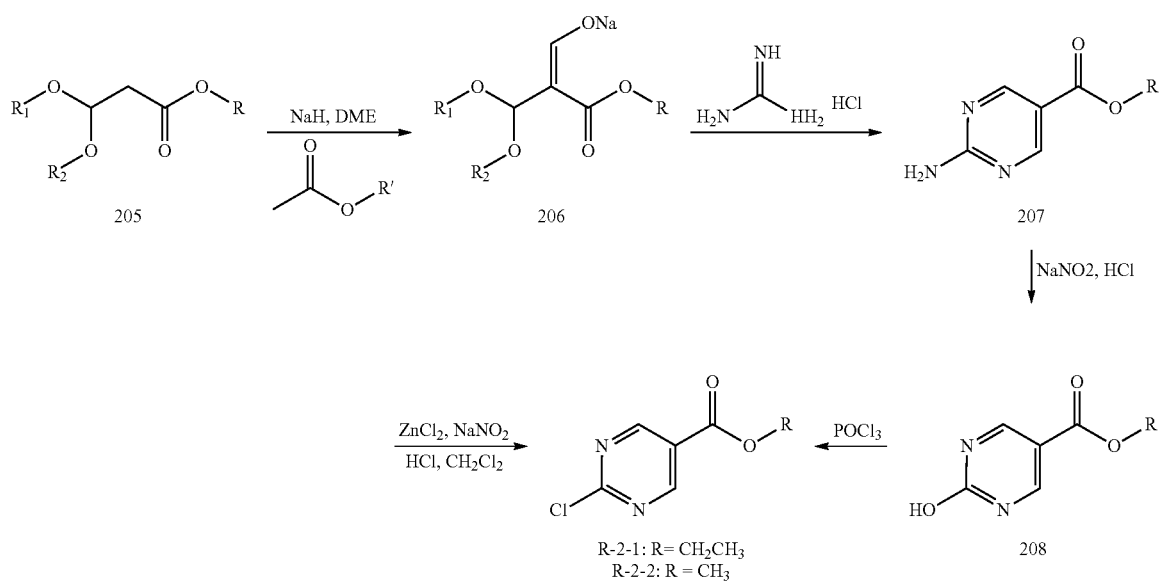
Intermediate 108-1 and 108-2 can be prepared by the coupling reaction of 107-1 or 107-2 with either R-3-1 or R-3-2, where R-3-1 and R-3-2 can be prepared according to the following scheme:
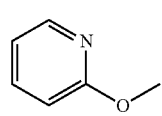
301
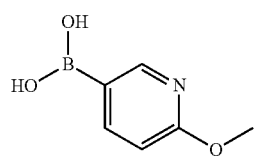
R-3-1

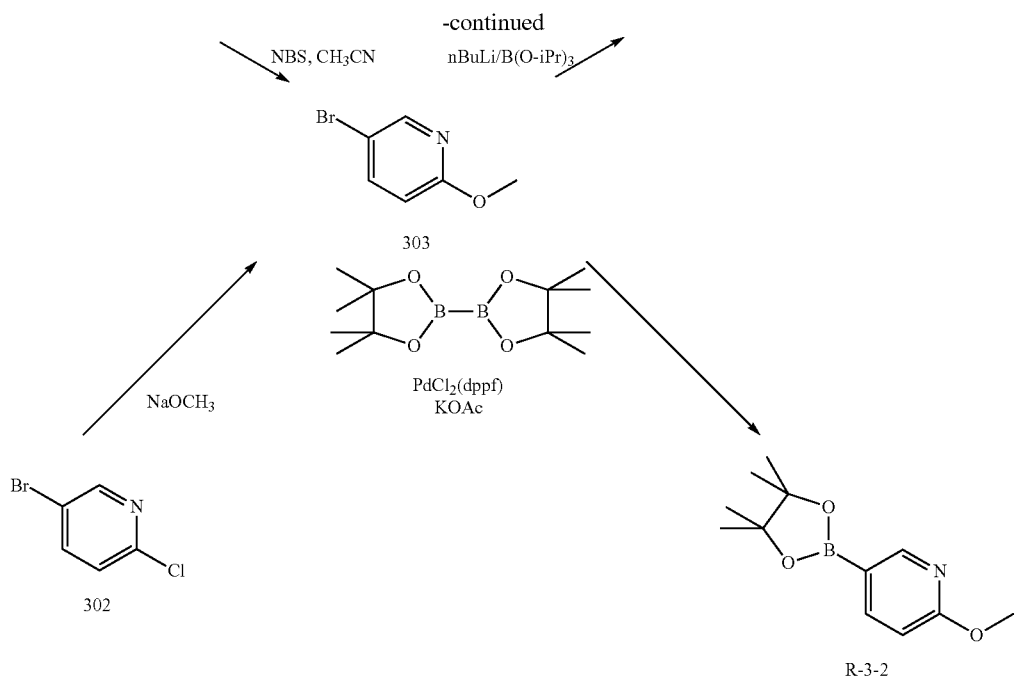

Example 1

Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide (Compound 1)

Step a: (Z)-Ethyl-2-(ethoxymethyl)-3-methoxyacrylate (Compound 202)

Sodium (40.9 g, 1.78 mol) was added to ethanol (750 mL) in portions carefully and the solution was concentrated to give NaOEt powder after all sodium metal disappeared. Under stirring, hexane (1.0 L) was added and the mixture was cooled with ice-water bath. A mixture of 201 (130 g, 0.89 mol) and ethyl formate (131 g, 1.78 mol) was added dropwise at 0-5° C. The reaction mixture was stirred at room temperature overnight. Dimethyl sulfate (224 g, 1.78 mol) was added dropwise with cooling of ice-water bath. The resulting mixture was heated at 50° C. for 2 h. To the mixture was added triethylammonium chloride (122 g) and sodium hydroxide (20 g). The mixture was then stirred at room temperature for 4 h and filtered. The filtrate was washed with water and dried over $Na_2SO_4$. It was concentrated to afford the titled compound (140 g, 37%) as a colorless oil which was used in the next step without further purification.

Step b: Ethyl 2-oxo-1,2,3,4-tetrahydropyrimidine-5-carboxylate (Compound 203)

A mixture of compound 202 (140 g, 0.745 mol), urea (40.0 g, 0.697 mol) and concentrated hydrochloric acid (34 mL) in ethanol (500 mL) was heated at reflux overnight. After evaporating ~50% of volume of reaction, the resulting suspension was filtered, washed with small amount of ethanol, and dried to give compound 203 (47 g, 37%) as a white solid. LCMS: 171 [M+1]$^+$. $^1$H NMR (400 MHz, CDCl$_3$): δ 1.19 (t, J=7.2 Hz, 3H), 3.92 (s, 2H), 4.08 (q, J=7.2 Hz, 2H), 7.0 (s, 1H), 7.08 (d, J=6.0 Hz, 1H), 8.83 (d, br, J=4.8 Hz, 1H).

Step c: Ethyl 2-oxo-1,2-dihydropyrimidine-5-carboxylate (Compound 204)

To a solution of compound 203 (47 g, 280 mmol) in acetic acid (500 mL) was added bromine (49.0 g, 307 mmol). The mixture was heated at reflux for 2 h, cooled to room temperature, further cooled at 0-5° C. and filtered to give the title compound 204 as a yellow solid (38 g, 54%). LCMS: 169 [M+1]$^+$. $^1$H NMR (400 MHz, D$_2$O): δ 1.28 (t, J=7.2 Hz, 3H), 4.32 (q, J=7.2 Hz, 2H), 9.00 (br, s, 2H).

Step d: Ethyl 2-chloropyrimidine-5-carboxylate (Compound R-2-1)

A mixture of compound 204 (38.0 g, 153 mmol) and phosphoryl trichloride (300 mL) and N,N-dimethylaniline (3 mL) was heated at reflux for 2 h, cooled to room temperature and concentrated. The residue was quenched carefully with ice-water, adjusted pH to 7-8 with sodium carbonate and extracted with EtOAc. The combined organics were washed with ice-water and brine, dried over $Na_2SO_4$, evaporated, and purified by column chromatography (eluted with EtOAc/Hexanes, 10%) to afford compound R-2-1 (15 g, 52%) as a white solid.
LCMS: 187 [M+1]$^+$. $^1$H NMR (400 MHz, CDCl$_3$): δ 1.36 (t, J=7.5 Hz, 3H), 4.39 (q, J=7.5 Hz, 2H), 9.08 (s, 2H).

Step e: Sodium (Z)-2-(dimethoxymethyl)-3-methoxy-3-oxoprop-1-en-1-olate (Compound 206)

A mixture of NaH (27 g, 60% in mineral oil, 0.675 mol) in anhydrous 1,2-dimethoxyethane (300 mL) was heated to 40-50° C. and methyl 3,3-dimethoxy propionate (205) (100 g, 0.675 mol) was added dropwise. The resulting mixture was stirred for 0.5 h and anhydrous methyl formate (81 g, 1.35 mol) was added dropwise at 40-50° C. The resulting mixture was stirred at 40-50° C. (inner temperature) for 2 h before it was cooled to 0° C. The reaction mixture was allowed to warm to 25° C. slowly and stirred overnight. Et$_2$O (150 mL) was added and stirred for 30 min. The resulting suspension was filtered. The solid was washed with Et$_2$O (100 mL), collected and dried to afford the title compound 206 (82 g, 61%) as an off-white solid. LCMS (m/z): 130.8 [M+1]$^+$. $^1$HNMR (400 MHz, CD$_3$OD): δ 3.36 (s, 6H), 3.60 (s, 3H), 5.34 (s, 1H), 8.92 (s, 1H).

Step f: 2-Amino-pyrimidine-5-carboxylic acid methyl ester (Compound 207)

To a mixture of guanidine hydrochloride (42.2 g, 0.44 mol) in DMF (300 mL) was added compound 206 (80 g, 0.40 mol). The resulting mixture was heated at 100° C. for 1 h. The reaction mixture was filtered before cooled. The filter cake was washed with 50 mL of DMF and the combined filtrate was concentrated to leave a residue which was suspended in cold EtOH and washed with cold EtOH (50 mL) to afford the compound 207 (38 g, 61.5%) as a yellow solid. LCMS (m/z): 154.2 [M+1]$^+$, 195.1 [M+42]$^+$. $^1$H NMR (400 MHz, CD$_3$OD): δ 3.88 (s, 3H), 8.77 (s, 2H).

Step g: Methyl 2-chloropyrimidine-5-carboxylate (Compound R-2-2)

Compound 207 (7 g, 0.046 mol) was added to a mixture of concentrated hydrochloric acid (15.2 mL) and CH$_2$Cl$_2$ (60 mL). After cooling, ZnCl$_2$ (18.6 g, 0.138 mol) was added at 15-20° C. The mixture was stirred at 15-20° C. for 0.5 h and cooled to 5-10° C. NaNO$_2$ (9.5 g, 0.138 mol) was added portion wise while keeping the internal temperature 5-10° C. The reaction was continued for ~2 h. The reaction mixture was poured into ice-water (50 mL). The organic layer was separated and the aqueous phase was extracted with CH$_2$Cl$_2$ (30 mL*2). The combined organic extracts were concentrated to afford crude product (4.2 g). The crude compound was suspended in hexane (20 mL), heated at 60° C. for 30 minutes and filtered. The filtrate was concentrated to afford the title compound R-2-2 (3.5 g, 44.4%) as an off-white solid. LCMS (m/z): 214.1 [M+42]$^+$. $^1$HNMR (400 MHz, CDCl$_3$): δ 4.00 (s, 3H), 9.15 (s, 2H).

Step h: 5-Bromo-2-methoxypyridine (Compound 303)

A solution of 2-methoxy-pyridine (100 g, 0.92 mole), NBS (180 g, 1.0 mole) in acetonitrile (1.0 L) was stirred at reflux for 21 h. TLC showed that the reaction was complete. The reaction mixture was cooled to room temperature and concentrated. ~900 ml solvent was collected. The resulting suspension was filtered and washed with n-hexane (~400 mL). The filtrate was concentrated again to afford crude product. The crude product was distilled at reduced pressure (30° C./~0.3 mmHg) to afford the title compound as a clear oil (146 g, 84%). LCMS (m/z): 190.0 [M+1]$^+$. $^1$H NMR (400 MHz, CDCl$_3$): δ 3.90 (s, 3H), 6.65 (d, J=8.8 Hz, 1H), 7.62 (dd, J=8.8 Hz, 2.4 Hz, 1H), 8.19 (s, 1H).

Step i: 6-Methoxypyridin-3-ylboronic acid (R-3-1):

To a solution of compound 303 (20 g, 0.11 mole) in anhydrous THF (180 ml) was added dropwise n-BuLi (59 mL, 2M in THF) at −78° C., the resulting mixture was stirred for 1 h. Triisopropyl borate (37 mL) was added at −78° C. and the reaction mixture was warmed to room temperature and continued to stir overnight. TLC (hexanes/ethyl acetate=5:1) showed reaction complete. The mixture was adjusted pH to 3-4 with 4N HCl (90 ml). The precipitate was collected by filtration to afford crude compound R-3-1 (21 g, 128%). The crude compound R-3-1 (21 g) was dissolved in water (200 ml) and the solution was adjusted pH to 8-9 with concentrated ammonia solution, the precipitate was collected by filtration to afford the pure title compound R-3-1 as a white solid. (11 g, 67%). LCMS (m/z): 154.1 [M+1]$^+$. $^1$H NMR (400 MHz, DMSO-d$_6$): δ 3.86 (s, 3H), 6.76 (d, J=8.4 Hz, 1H), 7.99 (dd, J=8.4 Hz, 2.0 Hz, 1H), 8.05 (br, 2H), 8.52 (d, J=2.0 Hz, 1H).

Step j: 2-methoxy-5-(4,4,5,5,-tetramethyl-1,3,2-dioxaborolan-2-yl)pyridine (Compound R-3-2)

A mixture of compound 303 (55 g, 0.29 mol), 4,4,4',4',5, 5,5',5'-octamethyl-2,2'-bi(1,3,2-dioxaborolane) (90 g, 0.35 mol), potassium acetate (57 g, 0.58 mol) and bis(triphenylphosphine)palladium(II) chloride (2.2 g, 3 mmol) in anhydrous dioxane (500 mL) was heated at 108° C. under N$_2$ atmosphere overnight. The reaction mixture was concentrated and purified by column chromatography eluted with hexanes/ethyl acetate to afford title compound R-3-2 (58 g, 84%). $^1$H NMR (400 MHz, DMSO-d$_6$): δ 1.30 (s, 12H), 3.88 (s, 3H), 6.81 (d, J=8.0 Hz, 1H), 7.88 (dd, J=8.0 Hz, 2.0 Hz, 1H), 8.41 (d, J=2.0 Hz, 1H).

Step k: Thieno[3,2-d]pyrimidine-2,4(1H,3H)-dione (Compound 102)

Urea Method:
A mixture of methyl 3-aminothiophene-2-carboxylate (101) (90.0 g, 573 mmol, 1.0 eq) and urea (277.6 g, 4.6 mol, 8.0 eq) was heated at 190° C. for 3-4 h and cooled to room temperature. To the reaction mixture was added aq. NaOH (10%, 800 mL). After stirring at ambient temperature for 1 h, the solid was removed by filtration. The filtrate was acidified with HCl to pH 3-4, the precipitated solid was collected by filtration, washed with water and dried in vacuo to give the desired product compound 102 as an off-white solid (87 g, 89%). m.p.: 280-285° C. LCMS (m/z): 169.0 [M+1]$^+$. $^1$H NMR (400 MHz, DMSO-d$_6$): δ 6.92 (d, J=5.2 Hz, 1H), 8.05 (d, J=5.2 Hz, 1H), 11.0-11.5 (br, 2H).

KOCN Method:
To a mixture of 3-aminothiophene-2-carboxylate (101) (100.0 g, 636.9 mmol, 1.0 eq), acetic acid (705 mL) and water (600 mL) was added a solution of potassium cyanate (154.8 g, 1.91 mol, 3.0 eq) in water (326 mL) slowly over a period of 1 h. The resulting mixture was stirred at room temperature for 20 h, filtered and rinsed with water (500 mL). The cake was charged to a suitably sized reactor and 2 M aqueous sodium hydroxide solution (1.65 L) was added, the slurry was stirred for 2 h and LCMS confirmed the formation of the desired product. The mixture was cooled to 10° C. and 3 M aqueous hydrochloric acid (1.29 L) was added until the pH=5.0-6.0. The slurry was filtered, rinsed with water (700 mL), and dried in vacuum oven at 50° C. for 24 h to afford compound 102 (100 g, 94%) as an off-white solid. LCMS (m/z): 169.1 [M+1]$^+$. $^1$H NMR (400 MHz, DMSO-d$_6$): δ 6.92 (d, J=5.2 Hz, 1H), 8.04 (d, J=5.2 Hz, 1H), 11.14 (s, 1H), 11.51 (s, 1H).

Step l: 2,4-Dichlorothieno[3,2-d]pyrimidine (Compound 103)

Phosphorous oxychloride (152 mL, 1.67 mol, 7.0 eq) was added slowly to cold solution of compound 102 (40 g, 238 mmol, 1.0 eq) and N,N-dimethylaniline (22.5 mL, 179 mmol, 0.75 eq) in acetonitrile (250 mL) while maintaining the temperature below 20° C. The mixture was then heated to 85° C. and stirred for 24 h. The reaction mixture was cooled to 15° C., and then poured slowly onto a mixture of ice and cold water (360 mL). The resulting slurry was filtered, rinsed with cold water (200 mL). The cake was dried in vacuum oven at 40° C. for 24 h to afford compound 103 (40.5 g, 83%) as an off-white solid. M.p.: 245-250° C.

LCMS (m/z): 205.0 [M+1]$^+$. $^1$H NMR (400 MHz, DMSO-d$_6$): δ 7.75 (d, J=5.2 Hz, 1H), 8.71 (d, J=5.2 Hz, 1H).

Step m: 2-Chloro-4-morpholinothieno[3,2-d]pyrimidine (Compound 104)

To a mixture of compound 103 (34.2 g, 167 mmol, 1.0 eq) and methanol (500 mL) was added morpholine (31.2 mL, 367 mmol, 2.2 eq) slowly. The reaction mixture was stirred at room temperature overnight. The precipitate was collected by filtration, washed with methanol and dried in vacuo to give the desired product compound 104 as a light-yellow solid (39 g, 91%). M.p.: 250-255° C. LCMS (m/z): 256.0 [M+1]$^+$. $^1$H NMR (400 MHz, DMSO-d$_6$): δ 3.76 (t, J=5.2 Hz, 4H), 3.92 (t, J=5.2 Hz, 4H), 7.42 (d, J=5.2 Hz, 1H), 8.32 (d, J=5.2 Hz, 1H).

Step n: 2-Chloro-4-morpholinothieno[3,2-d]pyrimidine-6-carbaldehyde (Compound 105)

To a suspension of compound 104 (20 g, 78.4 mmol, 1.0 eq) in THF (anhydrous, 320 mL) at −78° C. was added n-BuLi (in hexanes, 2.4 M, 40.8 mL, 102 mmol, 1.3 eq) slowly under nitrogen. The resulting slurry was allowed to warm up to −60° C. to turn into a clear brown solution. The reaction mixture was then cooled to −78° C. again and DMF (anhydrous, 9.1 mL, 118 mmol, 1.5 eq) was added slowly. The resulting solution was stirred at −78° C. for 0.5 h, warmed up to 0° C. over 1 h and was poured slowly to a mixture of aq HCl (0.25 M, 660 mL) and ice water (320 mL). The resulting slurry was stirred at 0-10° C. for 0.5 h, filtered, washed with cold water and dried in vacuo to afford compound 105 as a yellow solid (22 g, 98%). M.p.: 260-265° C. LCMS (m/z): 284.0 [M+1]$^+$ $^1$H NMR (400 MHz, DMSO-d$_6$): δ 3.77 (t, J=5.2 Hz, 4H), 3.96 (t, J=5.2 Hz, 4H), 8.30 (s, 1H), 10.21 (s, 1H).

Step o: (2-Chloro-4-morpholin-4-yl-thieno[3,2-d]pyrimidin-6-ylmethyl)-methyl-amine (Compound 106)

To a solution of compound 105 (20.0 g, 70.4 mmol, 1.0 eq) in methanol (125 mL) was added methylamine solution in methanol (27% v/v, 75 mL, 563.2 mmol) under nitrogen atmosphere. The reaction mixture was stirred at room temperature overnight and the solvent was removed in vacuo to give a crude solid product, which was dissolved in methanol (550 mL) and THF (220 mL) under nitrogen. Sodium borohydride (8 g, 211.2 mmol) was added in portions and reaction mixture was stirred at room temperature overnight. The reaction mixture was evaporated in vacuo and water (300 mL) was added. The aqueous mixture was extracted with methylene chloride and the combined extracts were dried over Na$_2$SO$_4$ and concentrated. The residue was dissolved in 6M HCl (230 mL) and stirred for 30 min. The aqueous solution was washed with methylene chloride for several times, and adjusted to pH 9-10 with NaOH (4N). The precipitated solid was collected by filtration and dried (60° C., 6 h) to give a light yellow solid (18 g, 85%). M.p.: 240-245° C. LCMS (m/z): 299 [M+1]$^+$. $^1$H NMR (400 MHz, DMSO-d$_6$): δ 2.32 (s, 3H), 3.74 (t, J=5.2 Hz, 4H), 3.88 (t, J=5.2 Hz, 4H), 3.96 (s, 2H), 7.24 (s, 1H).

Step p(a): 2-[(2-Chloro-4-morpholin-4-yl-thieno[3,2-d]pyrimidin-6-ylmethyl)-methyl-amino]-pyrimidine-5-carboxylic acid ethyl ester (Compound 107-1)

To a mixture of 106 (10 g, 33.6 mmol) and R-2-1 (6.8 g, 36.4 mmol) in CH$_3$CN (400 mL) at room temperature was added diisopropylethylamine (220 mL, 1.26 mol). The resulting mixture was stirred at room temperature overnight. The mixture was then evaporated and followed by the addition of methylene chloride (300 mL). The organic phase was washed with water, dried over Na$_2$SO$_4$ and concentrated in vacuo to leave a residue. To the residue was added ethyl acetate and the resulting mixture was stirred at ice/water bath temperature for 50 min. The resulting solid was collected by filtration to give the titled product 107-1 as a white solid (10.6 g, 70%). LCMS: 449 [M+1]$^+$. $^1$H NMR (400 MHz, DMSO-d$_6$): δ 1.30 (t, J=7.2 Hz, 3H), 3.25 (s, 3H), 3.71 (t, J=5.2 Hz, 4H), 3.83 (t, J=4.8 Hz, 4H), 4.29 (m, 2H), 5.21 (s, 2H), 7.39 (s, 1H), 8.87 (s, 2H).

Step p(b): 2-[(2-Chloro-4-morpholin-4-yl-thieno[3,2-d]pyrimidin-6-ylmethyl)-methyl-amino]-pyrimidine-5-carboxylic acid methyl ester (Compound 107-2)

A mixture of compound 106 (25 g, 84 mmol), CH$_3$CN (500 mL) and R-2-2 (16 g, 92 mmol) was stirred at room temperature. Diisopropylethylamine (DIPEA) (500 mL, 2.9 mol) was added. The solution was stirred overnight and evaporated. After methylene chloride (500 mL) was added, the organic phase was washed with water, dried with Na$_2$SO$_4$ and concentrated in vacuo. To the residue was added ethyl acetate (200 mL) and the mixture was stirred in ice/water bath for 50 min. The title product was collected as a white solid (29.4 g, 81%). LCMS (m/z): 435.2 [M+1]$^+$. $^1$HNMR (400 MHz, DMSO-d$_6$): 3.25 (s, 3H), 3.71 (t, J=5.2 Hz, 4H), 3.82-3.84 (m, 7H), 5.21 (s, 2H), 7.39 (s, 1H), 8.87 (s, 2H).

Step q(a): Ethyl-2-(((2-(6-methoxypyridin-3-yl)-4-morpholinothieno[3,2-d]pyrimidin-6-yl)methyl) (methyl)amino)pyrimidine-5-carboxylate (Compound 108-1)

Method A: A mixture of compound 107-1 (12 g, 26.7 mmol), R-3-1 (4.9 g, 32 mmol), NaHCO$_3$ (6.7 g, 80.1 mmol) and bis(triphenylphosphine)palladium(II) chloride (188 mg, 0.267 mmol) in a mixed solvents of toluene (80 ml), ethanol (50 ml) and water (10 ml) was heated at 108° C. for 4.5 h under N$_2$ atmosphere. TLC showed reaction was complete. The reaction mixture was then cooled to room temperature and water (20 ml) was added. The resulting solid was collected by filtration and was then suspended in ethanol (100 mL). The suspension was stirred at room temperature for 30 minutes and filtered. The collected solid was washed with ethanol and dried in vacuo to afford titled compound 108-1 as a white solid (10 g, 72%).

Method B: A mixture of compound 107-1 (1.5 g, 3.34 mmol), R-3-2 (1.6 g, 6.68 mmol), NaHCO$_3$ (0.84 g, 10.0 mmol) and bis(triphenylphosphine)palladium(II) chloride (118 mg, 0.167 mmol) in a mixed solvents of toluene (24 ml), ethanol (15 ml), and water (3 ml) was heated at 108° C. under N$_2$ atmosphere overnight. The reaction mixture was partitioned between dichloromethane and water. The organic layer was separated and was washed with brine, dried over Na$_2$SO$_4$, filtered and evaporated in vacuo to give a residue which was purified by column chromatography eluted with hexanes/ethyl acetate to afford compound 108-1 as a white solid (1.7 g, 98%).

m.p. 198-202° C. LCMS: 522.30 [M+1]$^+$. $^1$H NMR (400 MHz, DMSO-d$_6$): δ 1.31 (t, J=7.2 Hz, 3H), 3.28 (s, 3H), 3.76 (t, J=4.4 Hz, 4H), 3.93 (t, J=4.4 Hz, 4H), 3.94 (s, 3H), 4.30 (q, J=7.2 Hz, 2H), 5.24 (s, 2H), 6.92 (d, J=8.8 Hz, 1H), 7.47 (s, 1H), 8.57 (dd, J=8.8 Hz, 2.0 Hz, 1H), 8.88 (s, 2H), 9.15 (d, J=2.0 Hz, 1H).

Step q(b): Methyl-2-(((2-(6-methoxypyridin-3-yl)-4-morpholinothieno[3,2-d]pyrimidin-6-yl)methyl)(methyl)amino)pyrimidine-5-carboxylate (Compound 108-2)

To a mixture of compound 107-2 (20 g, 46.0 mmol), B-3-1 (9.2 g, 60.2 mmol, 1.3 eq.) in dioxane (540 mL) at room temperature was added solid NaHCO$_3$ (11.6 g, 138.1 mmol, 3 eq.) followed by the addition of water (40 mL). The resulting mixture was degassed by passing N$_2$ through surface of solution. Bis(triphenylphosphine) palladium(II) chloride (323 mg, 0.46 mmol, 0.01 eq.) was then added and the resulting mixture was heated at 108° C. for 15 h. TLC and LCMS showed reaction complete. The reaction mixture was filtered through Celite while it was still hot (>90° C.) and washed with dioxane (70 mL). The filtrate was cooled gradually to room temperature and white fine crystals formed during cooling period. The suspension was filtered and washed with dioxane (80 mL) to afford the titled compound 108-2 as a white solid (18 g, 78%). LCMS (m/z): 508.3 [M+1]$^+$. $^1$H NMR (400 MHz, DMSO-d$_6$): δ 3.28 (s, 3H), 3.76 (t, J=4.8 Hz, 4H), 3.82 (s, 3H); 3.92 (m, 4H), 3.93 (s, 3H), 5.20 (s, 2H), 6.91 (d, J=8.8 Hz, 1H), 7.47 (s, 1H), 8.57 (dd, J=8.8 Hz, 2.4 Hz, 1H), 8.88 (s, 2H), 9.15 (d, J=2.0 Hz, 1H).

Step r: N-Hydroxy-2-(((2-(6-methoxypyridin-3-yl)-4-morpholinothieno[3,2-d]pyrimidin-6-yl)methyl)(methyl)amino)pyrimidine-5-carboxamide (Compound 1)

Preparation of hydroxylamine methanol Solution

A mixture of NH$_2$OH.HCl (80 g, 1.12 mol) in MeOH (400 mL) was heated at 60-65° C. for 1 h to form a clear solution. It was then cooled in an ice-water bath. To the cold mixture was added a solution of KOH (96 g, 1.68 mol) in MeOH (240 mL) dropwise while maintaining the reaction temperature at 0-10° C. The resulting mixture was stirred at 0° C. for 30 minutes and then filtered through a constant pressure funnel filled with anhydrous Na$_2$SO$_4$ (700 g). The filtrate was collected under an ice-bath and stored in refrigerator for future use.

Preparation of Compound 1 from Compound 108-1

Compound 108-1 (10 g, 19 mmol) was suspended in the above freshly prepared hydroxylamine methanol solution (1.79M, 350 ml). To this mixture was added dichloromethane (100 mL). The reaction flask was sealed and the mixture was stirred at room temperature for 5 h before it turned into clear solution. Reaction was stirred for additional 9 h. and was filtered to remove any insoluble solid. The filtrate was adjusted to pH 6-7 with the addition of acetic acid to form solid precipitate. The solid was collected by filtration and washed with water and minimum amount of methanol, dried in vacuo at 60° C. for 5 h to afford compound 1 as a white solid (9.2 g, 96%). m.p. 177-180° C. LCMS: 509.3 [M+1]$^+$. $^1$H NMR (400 MHz, DMSO-d$_6$): δ 3.24 (s, 3H), 3.76 (t, J=5 Hz, 4H), 3.92 (t, J=5 Hz, 4H), 3.92 (s, 3H), 5.20 (s, 2H), 6.90 (d, J=8.8 Hz, 1H), 7.44 (s, 1H), 8.57 (dd, J=8.8 Hz, 2.4 Hz, 1H), 8.75 (s, 2H), 9.01 (s, 1H), 9.14 (d, J=2.0 Hz, 1H), 11.08 (s, 1H).

Preparation of Compound 1 from Compound 108-2

To a suspension of compound 108-2 (31 g, 61.1 mmol) in dichloromethane (310 mL) at room temperature was added above freshly prepared hydroxylamine methanol solution (1.79M, 744 ml). The reaction flask was sealed and the reaction mixture was stirred at room temperature for 5 h. The reaction mixture turned into a clear solution. The reaction solution was filtered to remove any insoluble solid. To the filtrate was then added water (310 mL) and there was no solid formed during the addition. Acetic acid (18.5 mL) was added to adjust pH to 10.20 (continuously monitored by pH meter) while stirring. There was no internal temperature change during acetic acid addition. The resulting reaction mixture was continued to stir for another 4 h. White solid gradually formed. The suspension was filtered and washed with minimum amount of methanol (100 mL×3). The collected white solid was re-suspended in methanol (620 mL) and water (124 mL) to form a suspension. To the above suspension was added additional acetic acid (11 g) to adjust the pH to 5-6. The change of the solid form was observed. The suspension was continued to stir for another 2 h and filtered through filter paper and washed with minimum amount of methanol (100 mL×3). The collected white solid was dried in oven (50° C.) for 12 h to afford the title Compound 1 as a white solid (23.6 g, 76.0%). m. p.: 255-259° C. LCMS (m/z): 509.3 [M+1]$^+$. $^1$H NMR (400 MHz, DMSO-d$_6$): δ 3.24 (s, 3H), 3.76 (t, J=5.2 Hz, 4H), 3.92 (t, J=5.2 Hz, 4H), 3.92 (s, 3H), 5.20 (s, 2H), 6.91 (d, J=8.4 Hz, 1H), 7.45 (s, 1H), 8.57 (dd, J=8.4 Hz, 2.4 Hz, 1H), 8.75 (s, 2H), 9.07 (s, 1H), 9.14 (d, J=2.4 Hz, 1H), 11.14 (s, 1H).

Example 2

Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide methanesulfonate (Compound 2)

Method A: To a mixture of Compound 1 (300 mg, 0.59 mmol) and MeOH/Et$_2$O (3/1, 40 mL) was added a solution of methanesulfonic acid (114 mg, 1.18 mmol) in MeOH (3 mL) at 0° C. The resulting mixture was stirred at 0° C. for 3 h. The precipitate was collected by filtration and washed with Et$_2$O to afford Compound 2 as a white solid (260 mg, 73%).

Method B: To a suspension of Compound 1 (1.5 g, 2.95 mmol) in dichloromethane/MeOH (40 mL/10 mL) was added methanesulfonic acid (341 mg, 3.55 mmol) in 2 mL MeOH at room temperature (15° C.) to form a clear solution. The reaction mixture was stirred at room temperature overnight. The reaction mixture was still clear. Ethyl acetate (40 mL) was added to the mixture and continued to stir for 3 h at room temperature. The resulting precipitate was collected by filtration to afford Compound 2 as a white solid (1.45 g, 83%).

m.p.: 179-185° C. LCMS: 509.3 [M+1]$^+$. $^1$H NMR (400 MHz, DMSO-d$_6$): δ 2.35 (s, 3H), 3.26 (s, 3H), 3.78 (t, J=9.6 Hz, 4H), 3.95 (s, 3H), 4.03 (t, J=9.2 Hz, 4H), 5.24 (s, 2H), 6.99 (d, J=8.8 Hz, 1H), 7.50 (s, 1H), 8.54 (dd, J=8.8 Hz, 2.4 Hz, 1H), 8.76 (s, 2H), 9.12 (d, J=2.4 Hz, 1H), 11.11 (br, 1H).

Example 3

Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide sodium salt (Compound 3)

To a suspension of Compound 1 (300 mg, 0.59 mmol) in methanol (30 mL) at 0° C. was added slowly t-BuONa (85 mg, 0.88 mmol). The resulting mixture was warmed to room temperature and continued to stir for 2 h. The reaction was concentrated and the residue was triturated and washed with ethanol followed by filtration to afford Compound 3 as a white solid (230 mg, 73%). m.p.: 178-183° C. LCMS: 509.3 [M+1]$^+$. $^1$H NMR (400 MHz, DMSO-d$_6$): δ 3.17 (s, 3H), 3.75 (s, 4H), 3.92 (s, 7H), 5.16 (s, 2H), 6.90 (d, J=8.4 Hz, 1H), 7.42 (s, 1H), 8.57 (d, J=8.0 Hz, 1H), 8.65 (s, 2H), 9.14 (s, 1H).

Example 4

Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide potassium salt (Compound 4)

To a mixture of Compound 1 (400 mg, 0.78 mmol) in methanol (50 mL) was added t-BuOK (132 mg, 1.17 mmol) at 0° C. under N$_2$. The mixture was stirred at 0° C. for 1 h and continued to stir at room temperature for 1.5 h. The insoluble solid was removed by filtration and the filtrate was cooled to −20° C. Et$_2$O (100 mL) was added to the filtrate. The resulting mixture was stirred at −20° C. for 1 h. Hexanes (70 mL) was added and the mixture was continued to stir at −20° C. for 2 h. The solid was collected by filtration and dried in vacuo to afford Compound 4 as a white solid (150 mg, 35%). m.p.: 174-179° C. LCMS: 509.3[M+1]$^+$.

$^1$H NMR (400 MHz, DMSO-d$_6$): δ 3.16 (s, 3H), 3.74-3.76 (m, 4H), 3.90-3.93 (m, 7H), 5.15 (s, 2H), 6.90 (d, J=8.4 Hz, 1H), 7.43 (s, 1H), 8.39 (br, 1H), 8.58 (d, J=8.8 Hz, 1H), 8.62 (s, 2H), 9.15 (s, 1H).

Example 5

Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide choline salt (Compound 5)

To a solution of Compound 1 (200 mg, 0.39 mmol) in DCM/MeOH (60 mL/12 mL) was added choline hydroxide (106 mg, 0.39 mmol, 45% in MeOH). The mixture was stirred at room temperature for 2 h and was then concentrated to remove ~30 mL of the solvent. Ethyl acetate (60 mL) was added and the mixture was stirred at room temperature for 2 h. After a small amount of precipitation occurred, the mixture was concentrated to remove ~40 mL of the solvent and additional ethyl acetate (60 mL) was added. The mixture was stirred at room temperature for 2 h and filtered to afford Compound 5 as a white solid (180 mg, 76%).

m.p.: 181-185° C. LCMS: 509.3[M+1]$^+$. $^1$H NMR (400 MHz, DMSO-d$_6$): δ 3.11 (s, 9H), 3.17 (s, 3H), 3.40 (t, J=4.8 Hz, 2H), 3.75 (t, J=4.8 Hz, 4H), 3.84 (br, 2H), 3.90-3.93 (m, 7H), 5.15 (s, 2H), 6.89 (d, J=8.8 Hz, 1H), 7.41 (s, 1H), 8.57 (dd, J=8.8 Hz, 2.4 Hz, 1H), 8.64 (s, 2H), 9.14 (d, J=2.0 Hz, 1H).

Example 6

Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide sulfate (Compound 6)

To a suspension of Compound 1 (200 mg, 0.39 mmol) in DCM/MeOH (30 mL/7.5 mL) was added sulfuric acid (77 mg, 0.79 mmol, in 1 mL MeOH) to form a clear solution. The reaction mixture was stirred at room temperature overnight. The precipitation occurred and tert-butyl methyl ether (60 mL) was then added. The resulting mixture was continued to stir for 1 h at room temperature. The solid was collected by filtration to afford Compound 6 as a white solid (180 mg, 76%). M.p.: 243-246° C. LCMS: 509.3 [M+1]$^+$. $^1$H NMR (400 MHz, DMSO-d$_6$): δ 3.26 (s, 3H), 3.78 (t, J=4.8 Hz, 4H), 3.96 (s, 3H), 4.03 (t, J=4.4 Hz, 4H), 5.24 (s, 3H), 6.98 (d, J=8.4 Hz, 1H), 7.50 (s, 1H), 8.54 (dd, J=8.8 Hz, 2.4 Hz, 1H), 8.76 (s, 2H), 9.12 (d, J=2.0 Hz, 1H), 11.06 (br, 1H).

Example 7

PI3 Kinase Activity Assay

The following assays were used to determine the ability of Compound 1 to inhibit various isoforms and mutants of PI3K.

PI3Kα

PI3Kα activity was measured using ADP-Glo luminescent kinase assay. PI3Kα, a complex of N-terminal GST-tagged recombinant full-length human p110α and untagged recombinant full length human p85α were coexpressed in a Baculovirus infected Sf9 cell expression system. (GenBank Accession No. for p110α, U79143; for p85α, XM_043865). The proteins were purified by one-step affinity chromatography using glutathione-agarose. A competition assay was performed to measure the amount of ADP generated from ATP in the presence of purified recombinant PI3Kα (p110α/p85α) and PIP2. PI3Kα was incubated with 20 μM PIP2 substrate in the reaction buffer (50 mM HEPES, pH 7.4, 150 mM NaCl, 5 mM MgCl$_2$, 3 uM Naorthovanadate, 1 mM DTT, 10 μM ultra pure ATP and 0.5% DMSO) for 30 minutes at 30° C. The ADP generated in the reaction was then measured by the ADP-Glo Assay. The assay was performed in two steps; first an equal volume of ADP-GLO™ Reagent (Promega) was added to terminate the kinase reaction and deplete the remaining ATP. In the second step, the Kinase Detection Reagent was added, which simultaneously converts ADP to ATP. The newly synthesized ATP was measured using coupled luciferase/luciferin reaction. The IC$_{50}$ determined for Compound 1 in this assay was less than 100 nM.

The ability of Compound 1 to inhibit the PI3Kα mutants H1047R and E545K was also determined using the general procedure described above. The IC$_{50}$ determined for both mutants was less than 100 nm.

PI3Kβ

Activity of PI3Kβ was measured using time-resolved fluorescence resonance energy transfer (TR-FRET) assay utilizing homogenous time resolved fluorescence (HTRF) technology. PI3Kβ, a complex of N-terminal histidine-tagged recombinant full-length human p110β and untagged recombinant full length human p85α were coexpressed in a Baculovirus infected Sf21 cell expression system. (GenBank Accession No. for p110β, NM_006219; for p85α, XM_043865). The proteins are purified by one-step affinity chromatography using glutathione-agarose. A competition assay was performed to measure the amount of PIP3 generated from PIP2 in the presence of purified recombinant PI3Kbeta (p110β/p85α). PI3Kβ was incubated with 10 μM PIP2 substrate in the reaction buffer (20 mM HEPES, pH 7.5, 10 mM NaCl, 4 mM MgCl$_2$, 2 mM DTT, 10 μM ATP and 1% DMSO) for 30 minutes at 30° C. The reaction product was then mixed with a PIP3 detector protein, europium-labeled antibody, biotin-labeled PIP3 probe and allophycocyanin-labeled Streptavidin. A sensor complex is formed to generate a stable TR-FRET signal in the reaction mixture. This signal intensity decrease as biotin-labeled probe binding to the PIP3 detector is displaced by PIP3 produced by enzymatic activity and the amount of unbound biotin-labeled PIP3 probe in the mixture increases. TR-FRET signal was determined using microplate reader with background subtraction.

The IC$_{50}$ determined for Compound 1 in this assay was between 100 and 1000 nM.

PI3Kδ

Activity of PI3Kδ was measured using fluorescence polarization assay. P131δ, a complex of N-terminal histidine-tagged recombinant full-length human p110δ and untagged recombinant full length human p85α were coexpressed in a Baculovirus infected Sf9 cell expression system. (GenBank Accession No. for p110δ, NM_005026). The proteins are purified by one-step affinity chromatography using glutathione-agarose. A competition assay was performed to measure the amount of PIP3 generated from PIP2 in the presence of purified recombinant PI3Kδ (p110δ/p85α). PI3Kδ was incubated with 10 μM PIP2 substrate in the reaction buffer (20 mM HEPES (pH 7.5), 10 mM NaCl, 4 mM MgCl$_2$, 2 mM DTT, 10 μM ATP and 1% DMSO) for 1 hour at 30° C. The reaction product was then mixed with a PIP3 detector protein and the fluorescent PIP3 probe. Polarization (mP) values decrease as fluorescent probe binding to the PIP3 detector is displaced by PIP3 produced by enzymatic activity and the amount of unbound fluorescent probe in the mixture increases. Polarization degrees (mP) value was determined using microplate reader with background subtraction.

The IC$_{50}$ determined for Compound 1 in this assay was less than 100 nM.

PI3Kγ

Activity of PI3Kγ was measured using time-resolved fluorescence resonance energy transfer (TR-FRET) assay utilizing homogenous time resolved fluorescence (HTRF) technology. N-terminal histidine tagged human PI3Kγ was expressed in a Baculovirus infected Sf9 cell expression system. (GenBank Accession AF327656). The proteins are purified by one-step affinity chromatography using glutathione-agarose. A competition assay was performed to measure the amount of PIP3 generated from PIP2 in the presence of purified recombinant PI3Kγ (p120γ). PI3Kγ (2 nM) was incubated with 10 μM PIP2 substrate in the reaction buffer (20 mM HEPES, pH 7.5, 10 mM NaCl, 4 mM MgCl$_2$, 2 mM DTT, 10 μM ATP and 1% DMSO) for 30 minutes at 30° C. The reaction product was then mixed with a PIP3 detector protein, europium-labeled antibody, biotin-labeled PIP3 probe and allophycocyanin-labeled Streptavidin. A sensor complex is formed to generate a stable TR-FRET signal in the reaction mixture. This signal intensity decrease as biotin-labeled probe binding to the PIP3 detector is displaced by PIP3 produced by enzymatic activity and the amount of unbound biotin-labeled PIP3 probe in the mixture increases. TR-FRET signal was determined using microplate reader with background subtraction.

The IC$_{50}$ determined for Compound 1 in this assay was between 100 and 1000 nM.

Example 8

HDAC Activity Assay

HDAC inhibitory activity was assessed using the Biomol Color de Lys system (AK-500, Biomol, Plymouth Meeting, Pa.). Briefly, HeLa cell nuclear extracts were used as a source of HDACs. Different concentrations of test compounds were serially diluted in dimethylsulfoxide (DMSO) and added to HeLa cell nuclear extracts in the presence of a colorimetric artificial substrate. Final assay condition contained 50 mM Tris/Cl, pH 8.0, 137 mM NaCl, 2.7 mM KCl and 1 mM MgCl$_2$. Reactions were carried in room temperature (25° C.) for 1 hour before addition of developer for termination. Relative enzyme activity was measured in the WALLAC Victor II 1420 microplate reader as fluorescence intensity (excitation: 350-380 nm; emission: 440-460 nm). Data were analyzed using GraphPad Prism (v4.0a) with a sigmoidal dose response curve fitting for IC$_{50}$ calculation. The IC$_{50}$ determined for Compound 1 in this assay was less than 100 nM.

The activities of Compound 1 against HDAC isotypes were also determined. HDAC specificity assays were performed at BPS Bioscience (San Diego, Calif.), following their standard operating procedure. Briefly, purified flag- (human HDAC-1), NCOR2- (human HDAC3), GST- (human HDAC4, 6, 7, 10 and 11) or His- (human HDAC 2, 5, 8 and 9) tagged enzymes were expressed in Sf9 insect cells and purified before use. The substrate used for HDAC1, 2, 3, 6, 7, 8, 9 and 11 was HDAC Substrate 3 developed by BPS Bioscience. For other HDAC enzymes, HDAC Class 2a substrate was used. All enzymatic reactions were conducted in duplicate at 37° C. for 30 minutes, except HDAC11 enzyme assay, which was conducted at room temperature for 3 hours.

The table below sets forth the results for each of HDACs 1-11, with IC$_{50}$ values provided as follows: I>1000 nM; 100 nM<II<1000 nM; 10 nM<III<100 nM; IV<10 nM.

| | HDAC | | | | | | | | | |
| --- | --- | --- | --- | --- | --- | --- | --- | --- | --- | --- |
| | 1 | 2 | 3 | 8 | 4 | 5 | 6 | 7 | 9 | 10 | 11 |
| IC$_{50}$ | IV | IV | IV | II | II | II | III | II | II | IV | IV |

Example 9

Cell Proliferation Assay

Human cancer cell lines were purchased from American Type Culture Collection (Manassas, Va.) and plated at 5,000 to 10,000 per well in 96-well flat-bottomed plates with culture medium, as suggested by the provider. The cells were then incubated with compounds at various concentrations for 72 hours in culture medium supplemented with 0.5% (v/v) fetal bovine serum (FBS). Growth inhibition was accessed by adenosine triphosphate (ATP) content assay using Promega CellTiter-Glo kit. Promega CellTiter-Glo kit is an ATP monitoring system based on firefly luciferase. Briefly, 16 μl of mammalian cell lysis and substrate solution was added to 84 μl of culture medium per well to lyse the cells and stabilize the ATP. The mixture was shaken and incubated for 30 minutes and subsequently the luminescence was measured. IC$_{50}$ values were calculated using PRISM software (GraphPad Software) with sigmoidal dose-response curve fitting.

Table 1 shows the antiproliferative activity in these cell-based assays of Compound 1 and reference compounds SAHA, GDC-0941 and the combination of SAHA and GDC-0941. In these assays, the following grading was used: I>10,000 nM, 10,000 nM≥II≥1000 nM, 1000 nM>III≥100 nM, 100 nM>IV≥10 nM, and V<10 nm for $IC_{50}$.

TABLE 1

| Cancer Type | Cell Line | SAHA | GDC-0941 | SAHA/GDC-0941 | Cmpd 1 |
|---|---|---|---|---|---|
| Colon | WiDr | II | I | III | IV |
|  | HCT116 | II | II | III | V |
|  | SW403 | II | I | II | V |
|  | SW620 | II | I | III | V |
|  | SWI-116 | II | I | II | V |
|  | T-84 | II | II | III | IV |
| NSCLC | H358 | II | II | II | V |
|  | H292 | II | II | III | V |
|  | H2122 | II | II | III | V |
|  | H460 | I | I | II | IV |
|  | A549 | II | II | II | IV |
|  | Calu6 | II | I | II | IV |
| Pancreas | MiaPaca2 | II | I | II | IV |
|  | CaPan2 | II | I | III | IV |
|  | CFPAC-1 | II | I | II | IV |
|  | PANC-1 | II | II | II | IV |
|  | SW1990 | II | I | II | V |
| Breast | HCC1500 | II | I | II | V |
|  | HCC1806 | II | I | II | IV |
|  | MDA-MB-231 | II | I | II | IV |
|  | SKBr3 | II | I | II | IV |
|  | BT474 | II | III | III | V |
|  | MDA-MB-361 | II | III | IV | V |
|  | UACC-893 | II | II | III | IV |
|  | MDA-MB-453 | III | III | III | V |
|  | MCF-7 | II | III | III | V |
|  | T47D | II | I | III | IV |
|  | ZR-75-1 | II | III | II | IV |
|  | MDA-MB-468 | II | III | II | IV |
| ALL | MOLT-4 | III | III | III | V |
|  | SUP-B15 | III | II | III | V |
| AML | HL-60 | III | III | III | V |
|  | U937 | III | II | III | V |
|  | THP-1 | I | II | III | IV |
|  | MV-4-11 | III | II | III | V |
| B-Cell | Pfeiffer | II | III | III | V |
| Lymphoma | Raji | II | I | II | IV |
|  | RL | III | II | III | V |
|  | DOHH2 | III | IV | IV | V |
|  | Granta 519 | II | I | III | V |
|  | Su-DHL4 | II | III | III | V |
|  | Daudi | II | I | III | IV |
| T-Cell | HH | III | III | III | V |
| Lymphoma | MJ | III | I | III | V |
|  | HuT78 | IV | III | IV | V |
| CML | K562 | II | II | III | IV |
|  | MEG-01 | II | I | II | V |
| Multiple | RPMI-8226 | II | I | III | V |
| Myeloma | OPM-2 | III | IV | III | V |
|  | ARH77 | II | I | III | V |

Example 10

Formulations of Compound 1 a. Compound 1 in 30% Captisol (10 mg/mL):

To a vial containing compound 1 (10 mg) was added 30% Captisol (0.937 ml). The mixture was sonicated for 2 min. To the mixture was added sodium hydroxide (1 N, 39.3 μA, 2 eq.) and sonicated/vortexed to give a clear solution (pH=12). The solution was then adjusted to pH=10 with hydrochloric acid (1 N, 23.6 μl, 1.2 eq.).

b. Compound 1 in 30% Captisol (7.5 mg/mL):

To a vial containing compound 1 (7.5 mg) was added 30% Captisol (0.941 ml). The mixture was sonicated for 2 min. To the mixture was added sodium hydroxide (1 N, 29.5 μA, 2 eq.) and sonicated/vortexed to give a clear solution (pH=12). The solution was then adjusted to pH=5 with hydrochloric acid (1 N, 29.5 μA, 2 eq.).

c. Compound 1 in C10/PEG1450/PEG400 (5 mg/mL):

To a vial containing compound 1 (5 mg), sodium decanoate (20 mg), PEG400 (40 μl), and PEG1450 (40 mg) was added $H_2O$ (0.88 ml) and NaOH (1 N, 24.6 μl, 2.5 eq.). The mixture was sonicated and vortexed to give a clear solution which was then adjusted to pH=10 with HCl (1 N, 7.4 μl, 0.75 eq.).

Example 11

Pharmacokinetics and Pharmacodynamics Studies in Tumor-Bearing Mice

Nude Mice Bearing H2122 Tumors

Nude mice bearing H2122 (human non-small cell lung cancer cell line) xenograft tumors were used for pharmacokinetics studies. Compound 1 was formulated in water with sodium decanoate and PEG400 (5 mg/ml) and was administered orally (PO) via gavage to each animal at a dose of 50 mg/kg. At various time points following compound administration, three mice per time point were euthanized with $CO_2$, and blood and tumor tissues were collected. Blood was collected into tubes containing sodium heparin. The plasma was separated via centrifugation. Plasma and tissues were stored at −80° C. for later analysis. A PE Sciex API-3000 LC-MS/MS system (Applied Biosystems, Inc., Foster City, Calif.) was used to analyze compound concentrations in plasma and tumor tissues.

The results of this study are summarized in FIG. 1 and Table 2, below. FIG. 1 is a graph of Compound 1 concentration in plasma and tumor tissue versus time following oral administration. The results show that Compound 1 preferentially accumulates in tumor tissue. This is supported by the results set forth in Table 3, which show a significantly longer half-life of Compound 1 in tumor tissue than in plasma as well as significantly greater exposure of tumor tissue to Compound 1 (AUC).

TABLE 2

| Parameter | Plasma | Tumor |
|---|---|---|
| Half-life (Hours) | 5.9 | 10.1 |
| $C_{max}$ (ng/mL) | 186 | 154 |
| Area under the Curve (ng/mL * hr) | 478 | 2126 |
| Bioavailability (%) | 7.8 | 14.8 |

SCID Mice Bearing Daudi Tumors

Daudi (non-Hodgkin's lymphoma cell line) cells were implanted into female Scid (severe complex immune-deficient) mice. Following establishment of tumors, animals were dosed by oral gavage with 25, 50 or 100 mg/kg Compound 1, formulated in 30% Captisol, pH 10, at a concentration of 1.875, 3.75 or 7.5 mg/mL, respectively.

At various time points following compound administration, three mice per time point were euthanized with $CO_2$, and blood and tumor tissues were collected. Blood was collected into tubes containing sodium heparin. The plasma was separated via centrifugation. Plasma and tissues were stored at −80° C. for later analysis. A PE Sciex API-3000 LC-MS/MS system (Applied Biosystems, Inc., Foster City, Calif.) was used to analyze compound concentrations in plasma.

Figure 2:
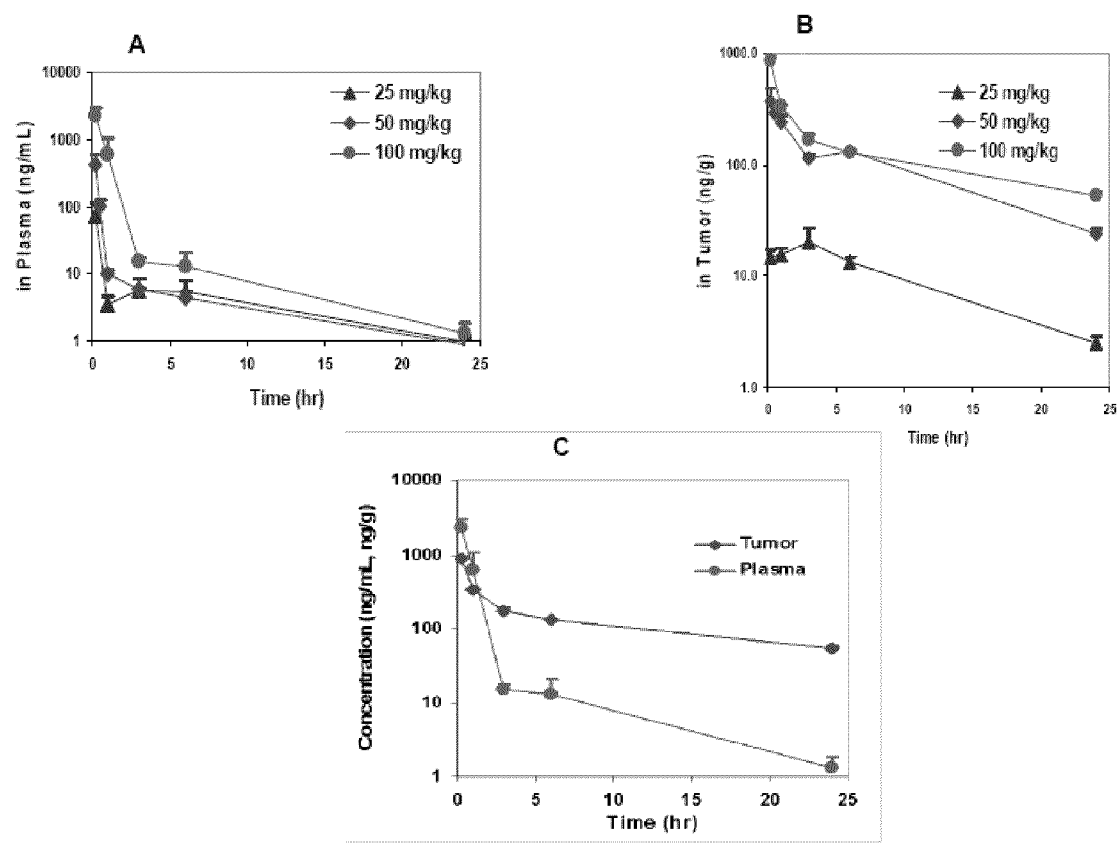
FIG. 2A is a graph of Compound 1 plasma concentration versus time in Daudi xenograft tumor-bearing Scid mice following oral dosing at 25, 50 and 100 mg/kg.
FIG. 2B is a graph of Compound 1 tumor concentration versus time in Daudi xenograft tumor-bearing Scid mice following oral dosing at 25, 50 and 100 mg/kg.
FIG. 2C is a graph of Compound 1 concentration versus time in plasma and tumor tissue in Daudi xenograft tumor-bearing Scid mice following oral dosing at 100 mg/kg.

The results of this study are summarized in FIGS. 2A, 2B and 2C and Table 3, below. FIG. 2A is a graph of Compound 1 concentration in plasma versus time following oral administration and shows a dose-dependent exposure to the compound. FIG. 2B is a graph of Compound 1 concentration in tumor tissue versus time following oral administration. The results show that Compound 1 preferentially accumulates in tumor tissue in a dose dependent manner. Plasma and tumor concentrations following the 100 mg/kg dose are compared in FIG. 2C, which shows that tumor tissue preferentially takes up Compound 1. This is supported by the results set forth in Table 3, which show a significantly longer half-life of Compound 1 in tumor tissue than in plasma as well as significantly greater exposure of tumor tissue to Compound 1 (AUC).

TABLE 3

| Parameter | Plasma | Tumor |
|---|---|---|
| Half-life (Hours) | 7.73 | 12.62 |
| $C_{max}$ (ng/mL) | 2285.39 | 1044.7 |
| Area under the Curve (ng/mL * hr) | 1899.26 | 3973.56 |
| $T_{max}$ (hr) | 0.24 | 0.10 |

Pharmacodynamics

Tumors were collected for PD evaluation following treatment with a single dose of Compound 1 at 25 mg/Kg, 50 mg/kg and 100 mg/kg. Protein was extracted from tumor tissues using a Tissuelyser (Qiagen, Valencia, Calif.) according to the manufacturer's instructions. 30 ug of protein was routinely used for WB analysis as described above. Cell lysates were resolved on NuPAGE Novex 4-12% Bis-Tris gels (Invitrogen) and transferred to nitrocellulose membranes (Bio-Rad Laboratories, Hercules, Calif.). The blots were probed with various primary antibodies overnight at 4° C. GAPDH (glyceraldehyde 3-phosphate dehydrogenase, 1:30,000, Abcam, Cambridge, Mass.) was used as an internal control for each assay. Membranes were then incubated with infrared labeled secondary antibodies (1:10000) conjugated-IR Dye-800 (Rockland Immunochemicals, Inc. Gilbertsville, Pa.) or conjugated-Alexa 680 (Invitrogen). Membranes were imaged with the Odyssey Infrared Imaging System (Li-Cor Biotechnology, Lincoln, Nebr.).

Figure 3:
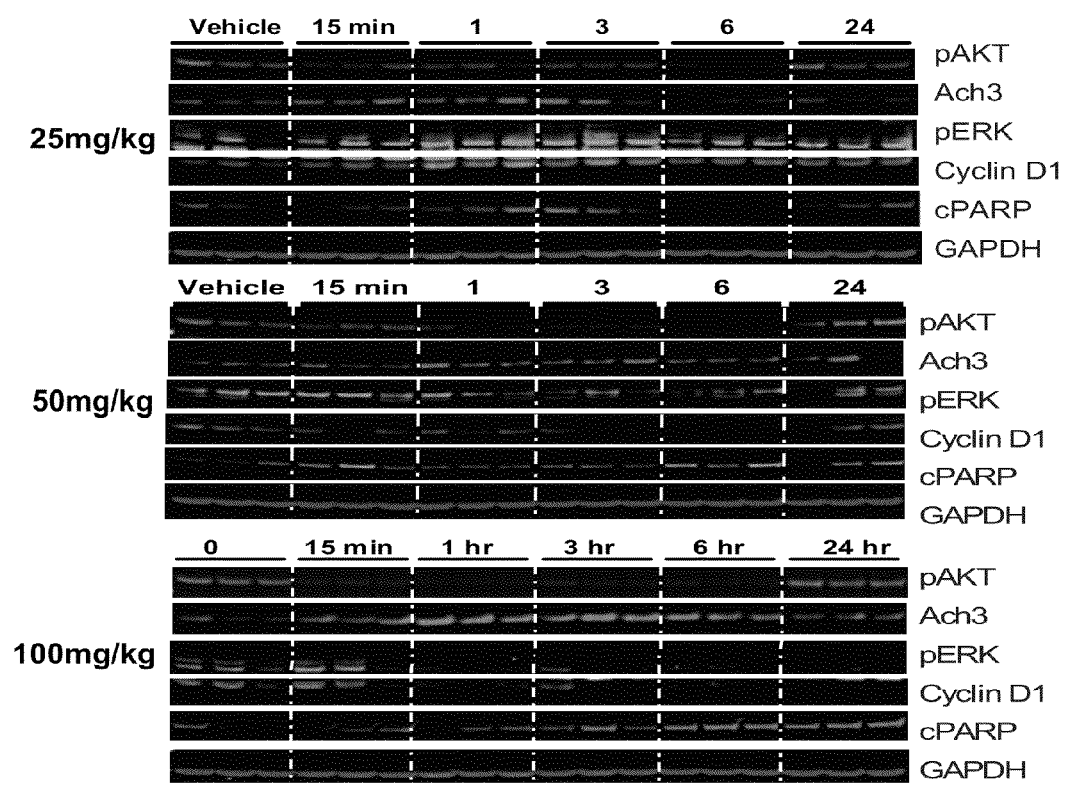
FIG. 3 presents Western blots of tumor tissue extracts from control and Compound 1 treated (25, 50 and 100 mg/Kg) Scid mice bearing Daudi tumor xenografts.

The results of this study are set forth in FIG. 3, which presents Western blots of tumor tissue extracts from the three dose groups. These results show that Compound 1 inhibits the PI3K-AKT-mTOR pathway, supresses the RAF-MEK-ERK pathways, downregulates RTK protein levels and up-regulates tumor suppressor p53 and p21 levels.

Example 12

Pharmacokinetic Study in Dogs

Figure 4:
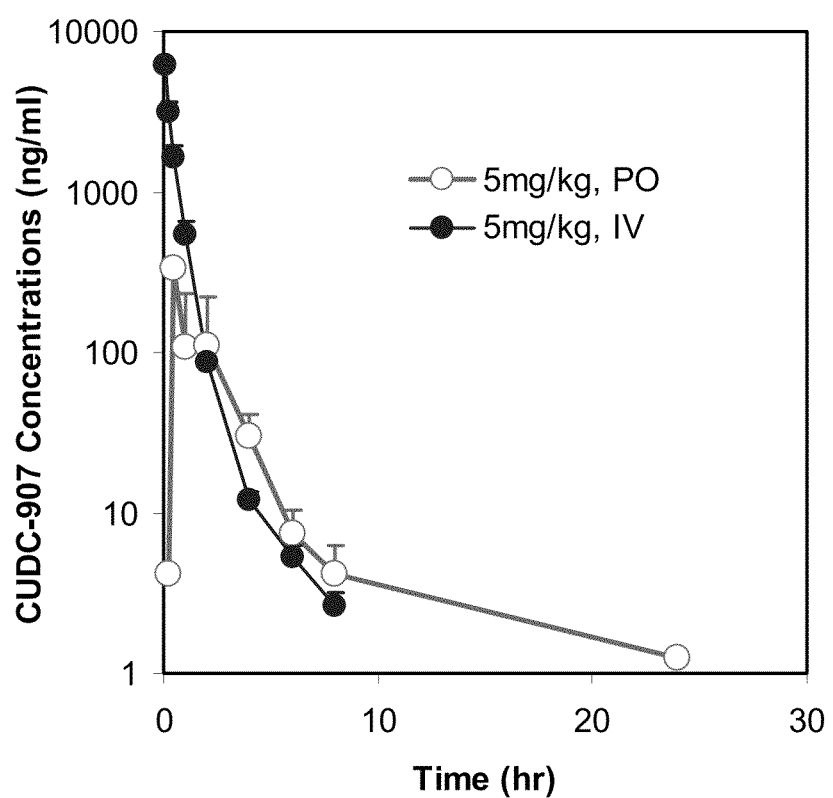
FIG. 4 is a graph of Compound 1 plasma concentration versus time in beagle dogs following oral or intravenous dosing.
Figure 5:
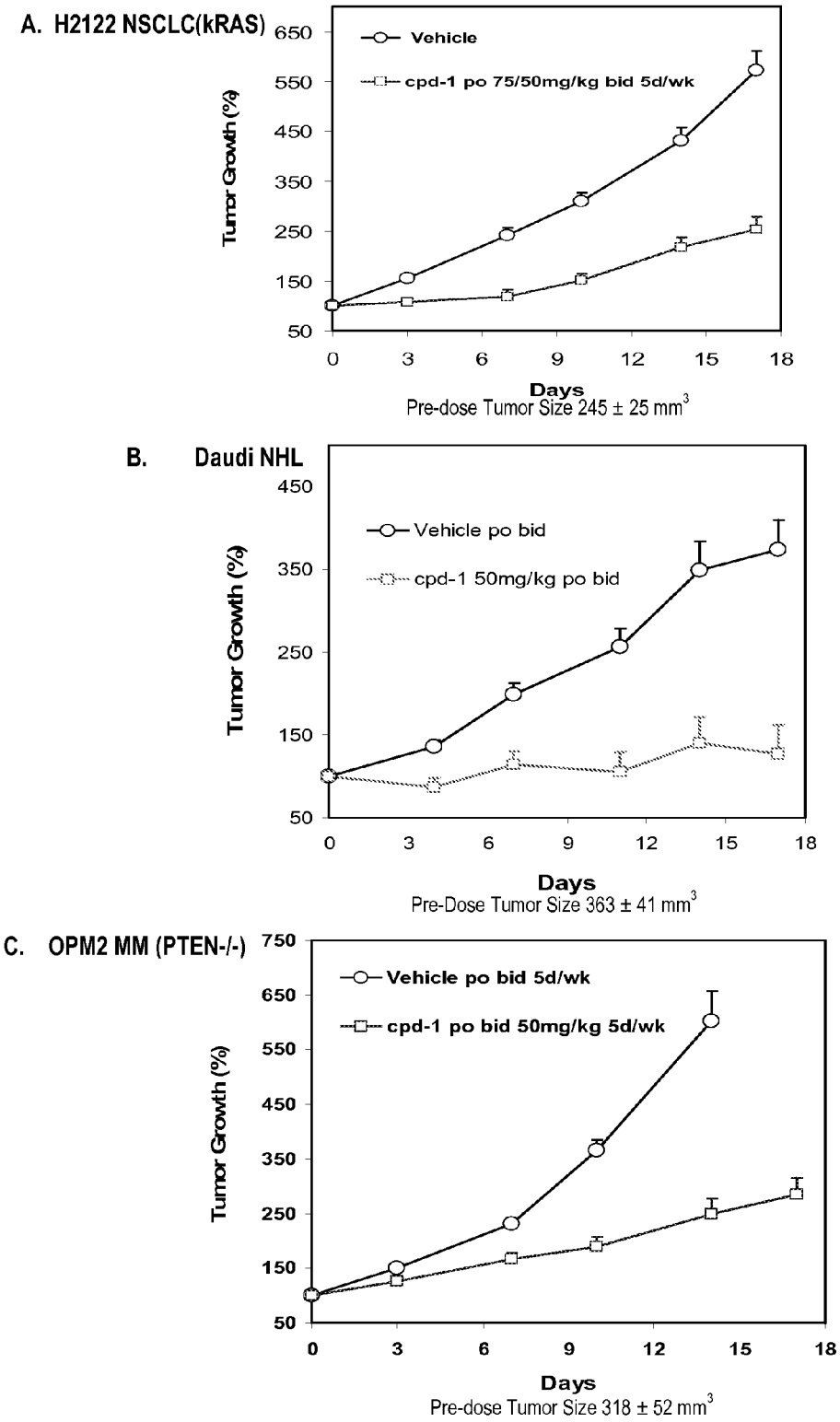
FIG. 5A is a graph of tumor growth versus time in H2122 xenograft tumor-bearing nude mice treated with Compound 1 or vehicle.
FIG. 5B is a graph of tumor growth versus time in Daudi xenograft tumor-bearing nude mice treated with Compound 1 or vehicle.
FIG. 5C is a graph of tumor growth versus time in OPM2 xenograft tumor-bearing nude mice treated with Compound 1 or vehicle.

A pharmacokinetic study of Compound 1 in beagle dogs was also conducted using iv administration at 5 mg/kg in water with sodium decanoate/PEG400 (5 mg/ml) and oral administration at 5 mg/kg with sodium decanoate/PEG4000/PEG1450 (pH 10) in enteric capsules. Plasma was collected at various time points and analyzed for Compound 1 concentration by LC-MS/MS. The results of the study are shown in FIG. 4 and Table 4, below. FIG. 4 is a graph of plasma concentration versus time for both oral and iv dosing. Significant plasma levels of Compound 1 are achieved via oral dosing.

TABLE 4

| Parameter | IV | PO Capsule |
|---|---|---|
| Half-life (Hours) | 1.85 | 4.88 |
| $C_{max}$ (ng/mL) | 6156.16 | 312.1 |
| Area under the Curve (ng/mL * hr) | 2977.47 | 450.4 |
| Bioavailability (%) |  | 15.1 |

Example 13

Pharmacokinetic Study in Rats

The purpose of this study was to determine the plasma pharmacokinetics of Compound 1 in male Sprague-Dawley rats following oral administration of Compound 1.

Compound 1 was dissolved in 30% Captisol in water to yield a nominal concentration of 10 mg/mL (pH=10) for oral administration. The resulting clear yellow solution was stored at room temperature until picked up for dosing.

Three male Sprague-Dawley rats from Charles River Laboratories were used in this study. High fat diet (VHFD, D12492i) from Research Diets Inc. were provided ad libitum throughout the in-life portion of the study. Compound 1 was administered via a single oral (PO) gavage dose at 20 mg/kg.

Blood samples (approximate volume 150 μL) were collected tail vein at 0.25, 0.5, 1, 3, 6, and 24 hours postdose. Blood samples were placed into tubes containing sodium heparin and centrifuged at 8000 rpm for 6 minutes at 4° C. to separate plasma from the samples. Following centrifugation, the resulting plasma was transferred to clean tubes and stored frozen at −80° C. pending bioanalysis.

The concentrations of Compound 1 and its primary metabolite in the plasma samples were determined using a PE Sciex API-3000 LC-MS/MS system (PE-Sciex., Foster City, Calif.).

The pharmacokinetic parameters were determined from mean concentration-time data in the test subjects. A compartmental modeling of WINNONLIN® Professional 5.2. was used to calculate parameters. Any concentrations that were below the limit of quantitation (lower limit of quantitation=1 ng/mL) were omitted from the calculation of parameters in individual animals.

Following oral administration of Compound 1, the mean values of $C_{max}$ and $T_{max}$ for Compound 1 were 39.5 μg/L and 0.1 hr, respectively. The mean value of $AUC_{(0-\infty)}$ was 163.6 μg/L*hr. The value of half-life ($T_{1/2}$) was 11.7 hr.

Example 14

Evaluation of Compound 1 in Xenograft Tumor Models

A. SU-DHL4, H2122, Daudi and OPM2 Xenograft Tumor Models

SU-DHL4 (diffuse large B-cell lymphoma cell line), H2122 (human NSCLC cell line), Daudi (non-Hodgkin's lymphoma cell line), and OPM2 (multiple myeloma tumor cell line) cells were implanted into either nude or Scid (severe complex immune-deficient) mice. Following establishment of tumors, animals with sufficient tumor size were randomly assigned into active (Compound 1) and control (vehicle) groups. Compound 1 was formulated for oral administration as in Example 7(b), and delivered by oral gavage based on the body weight of each individual animal. The control groups were treated with vehicle using the same dosing schedule as the corresponding active group.

The H2122 tumor group (nude mice) received Compound 1 at doses of 75 mg/kg twice a day initially and then 50 mg/Kg twice a day from Day-11 for five days per week due to body weight loss at 75 mg/Kg. In one study, the Daudi tumor group (Scid mice) received Compound 1 at doses of 25, 50 or 100 mg/Kg five day per week. In another study, the Daudi tumor group was dosed at 50 mg/Kg twice a day for five days per week. In another study, the efficacy of orally administered Compound 1 in the Daudi tumor model was compared to oral GDC-0941 and oral vorinostat, both individually and in combination. The OPM2 tumor group received Compound 1 at doses of 50 mg/kg twice a day for five days per week. The SU-DHL4 tumor group was dosed at 100 mg/Kg orally or 50 mg/Kg intravenously.

Tumors were measured during the study period with an electronic caliper, and body weights were measured twice a week. The following formula was used to calculate the tumor volume:

$$\text{Tumor volume} = (\text{length} \times \text{width}^2)/2$$

Percentage of tumor volume change was used to describe compound activity over the treatment period.

Figure 10:
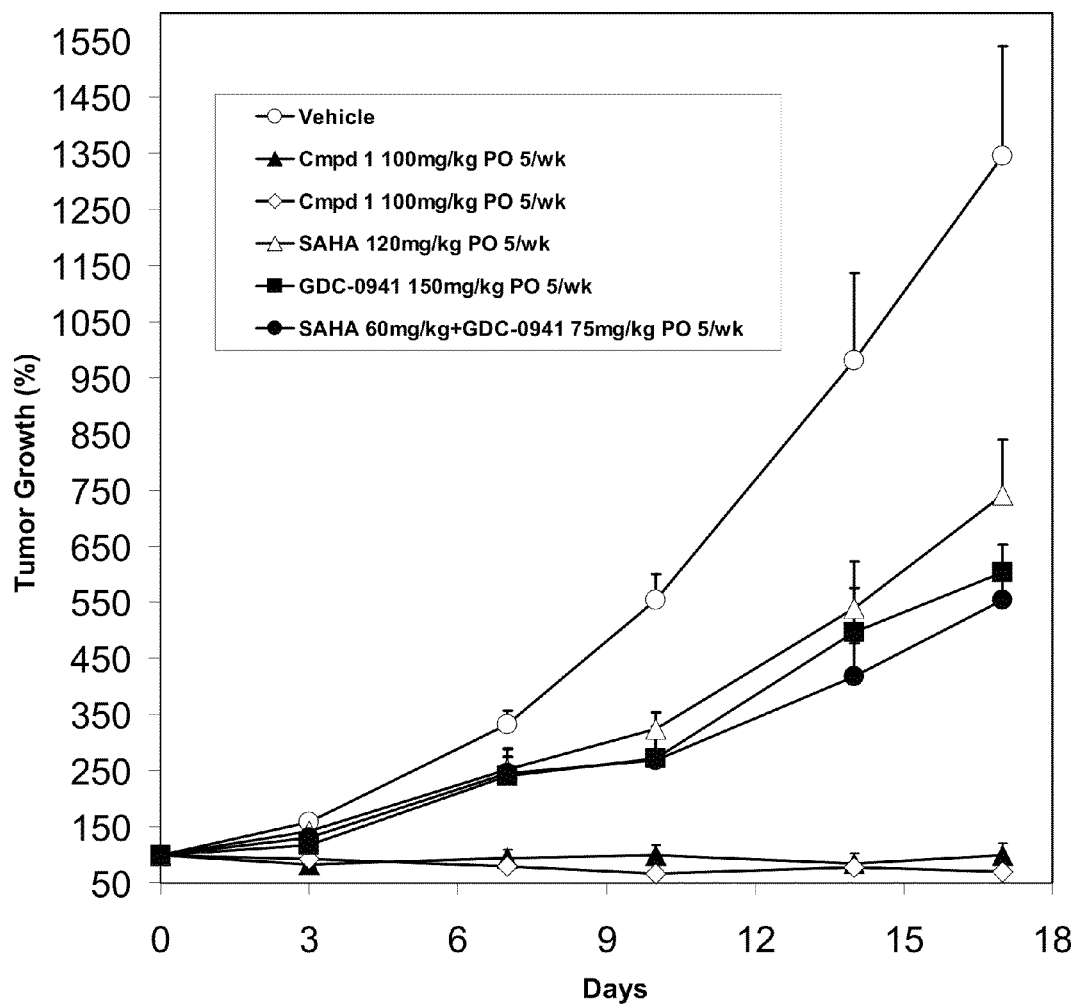
FIG. 10 is a graph of tumor growth versus time in Daudi xenograft tumor-bearing Scid mice treated with vehicle, Compound 1, SAH, GDC-0941 or a combination of SAHA and GDC-0941.
Figure 11:
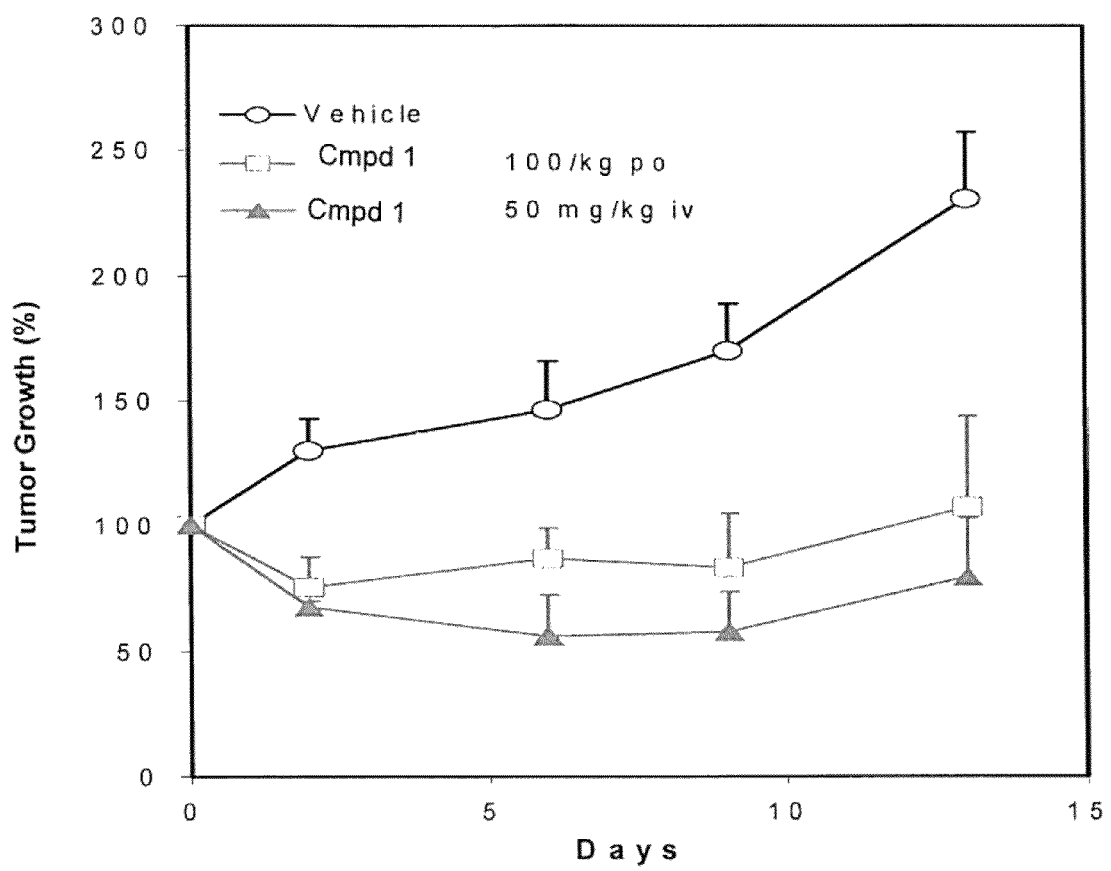
FIG. 11 is a graph of tumor growth versus time in SU-DHL4 xenograft tumor-bearing nude mice treated orally with Compound 1 or vehicle.
Figure 12:
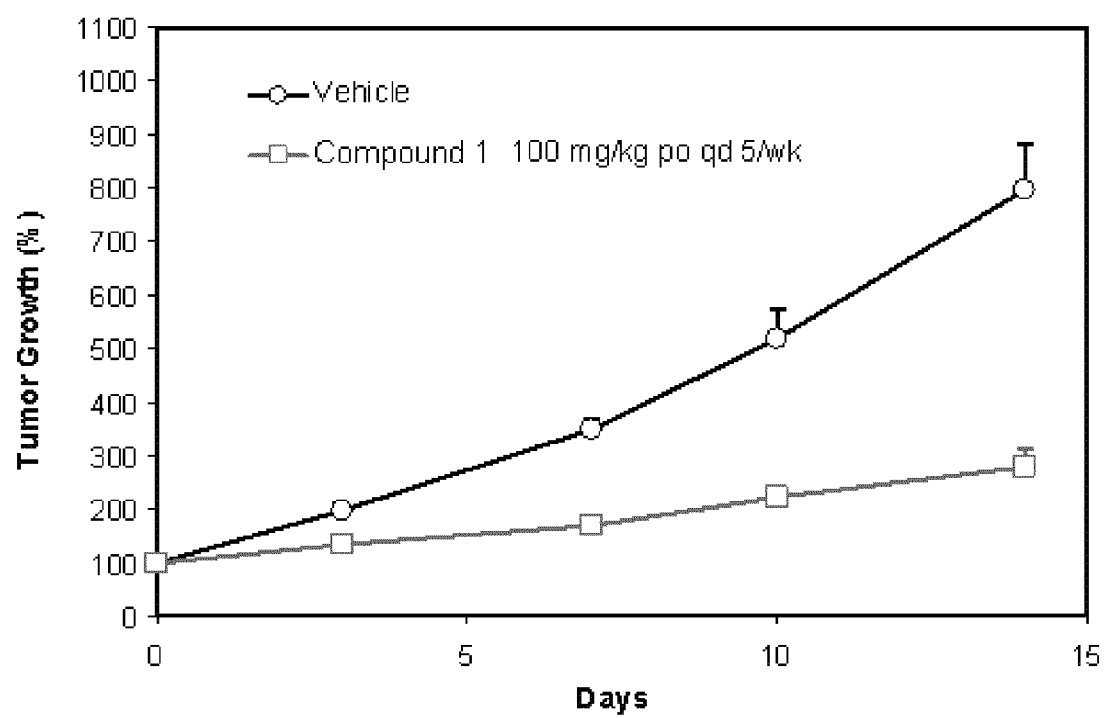
FIG. 12 is a graph of tumor growth versus time in OPM2 xenograft tumor-bearing nude mice treated with Compound 1 or vehicle.

The results of these studies are summarized in FIGS. 5A to 5C and 9 to 12, which show tumor size versus time for active and control groups for each of the tumor types. FIGS. 5A, 5B, 5C and 12 show that Compound 1 is efficacious in the H2122, Daudi and OPM2 tumor models. As set forth in FIG. 9, Compound 1 inhibited Daudi tumor growth in a dose-dependent manner. FIG. 10 compares the antitumor activity of Compound 1 at 100 mg/Kg in the Daudi model with either GDC-0941 or vorinostat alone or in combination. The indicated doses are the maximum tolerated dose (MTD) of each treatment, and the pretreatment tumor size was 157±65 mm$^3$ (mean±SE). The data indicate that Compound 1 is more efficacious than vorinostat, GDC-0941, or a combination of both. Finally, Compound 1 strongly inhibited tumor growth in the SU-DHL4 diffuse large B-cell lymphoma xenograft model following intravenous (IV) administration at 50 mg/kg or orally (PO) at 100 mg/kg (FIG. 11). The pretreatment tumor size was 147±21 mm$^3$.

MM1S Xenograft Model

Female SCID/Beige mice at age 4 weeks were housed in ventilated micro-isolator cages (INNOCAGE®IVC, Innovive Inc., San Diego, Calif.) in a controlled climate, fed with sterile high-fat diet (Problab-RMH 2000) ad libitum and provided with sterilized water. All housing and supplies for SCID/Beige mice were sterilized by autoclaving before use. Mice were inspected daily including weekends/holidays by trained animal facility personnel and investigators. All animal procedures were performed under sterile conditions within a biosafety cabinet (for injections) or laminar flow hood (for animal husbandry and non-invasive procedures).

MM1S human MM cells (Goldinan-Leikin R E, et al., *J Lab Clin Invest*. 1980; 113:335-345) were originally obtained from peripheral blood of a multiple myeloma patient. Cryopreserved cells were thawed in a 37° C. water bath and cultured in RPMI medium plus 10% Fetal Bovine Serum (FBS) in a tissue culture incubator at 5% $CO_2$. Cells were sent to outside vendors for contaminants and rodent pathogen screening intended to rule out contamination by mycoplasma (by PCR) and/or virus (by MAP test, Mouse Antibody Production). When the cells in culture were enough for implantation, they washed with serum free Hank's balanced salt solution (HBSS). Finally the cells were diluted in HBSS for implantation. Only single-cell suspensions of greater than 90% viability (by trypan blue exclusion) were used for injection and 20 million cells per animal suspended in 0.2 ml HBSS were injected subcutaneously in the right hind flank region of the mouse after a minimum 7 day acclimation period, using a 1 CC syringe with a 26 G hypodermic needle, taking care to avoid blood vessels. Successful implantation was indicated by the formation of a round, raised mass under the skin. The implanted mice were monitored for general health and tumor development daily.

Tumors were detectable about two weeks following implantation. Tumor size was measured with a caliper. The following formula was used to calculate the tumor volume:

$$\text{Tumor volume} = (\text{length} \times \text{width}^2)/2$$

Three weeks after tumor implantation, tumors reached an average of 194.6±37.9 mm$^3$. Animals with acceptable tumor size and shape were randomly assigned into two groups of eight animals each, using sorting software, one vehicle control and one treatment group.

Compound 1 was formulated and dosed as follows: 7.5 mg/ml was dissolved in 30% Captisol with 2 molar equivalents of NaOH and HCl each and dosed by oral gavage everyday five times per week based on body weight of each mouse. The control group was dosed with vehicle (30% Captisol) using same dosing paradigm.

During each animal study, tumors were measured with calipers, tumor size determined using the above mentioned formula, and tumor size changes in percentage calculated. Mouse body weights were measured with a scale twice per week. Studies were continued until either: a) the predetermined end date indicated in the study design; or b) the onset of health problems, whichever occurred first. In addition, the following tumor-related parameters warranted provision of euthanasia: (1) tumor burden exceeding 2500 mm$^3$ and/or (2) loss of ≥20% of starting body weight. In addition to the determination of tumor size changes, the last tumor measurement was used to generate the tumor weight change ratio (T/C value), a standard metric developed by the National Cancer Institute (NCI) for xenograft tumor evaluation T/C values were calculated using the following formula: % T/C=100× $\Delta T/\Delta C$ if $\Delta T>0$. In cases where tumor regression occurred, however, the following formula was used: % $T/T_0 = 100 \times \Delta T/T0$ if $\Delta T<0$.

The treatment period was 15 days. Tumor sizes and body weights were measured again on the last day of the study.

Figure 13:
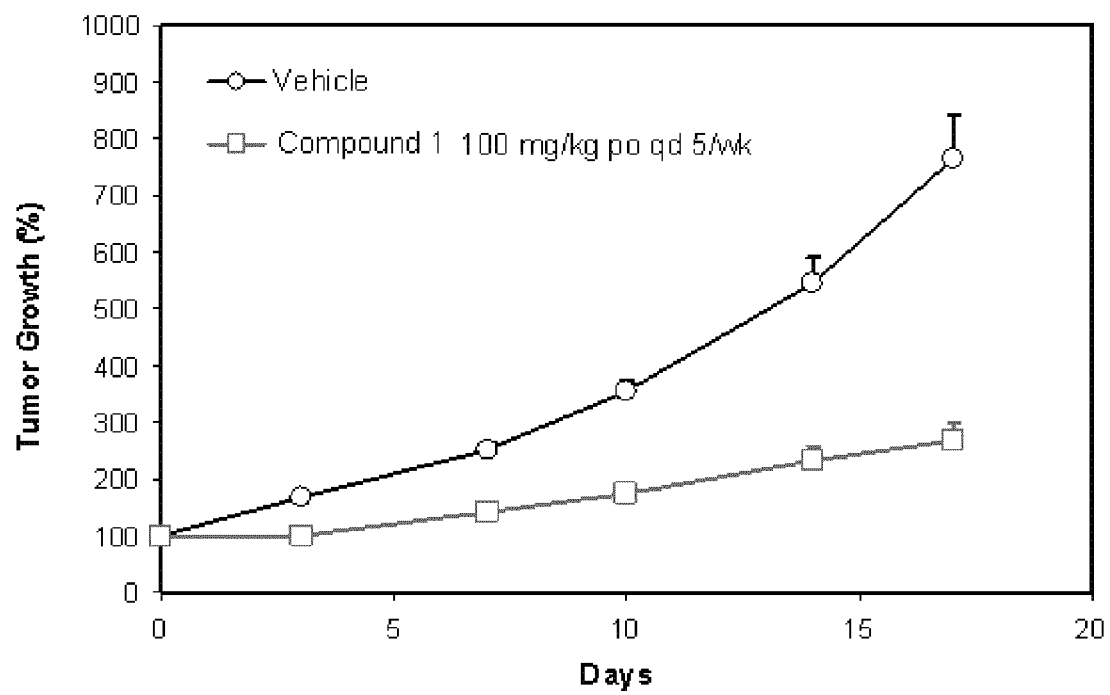
FIG. 13 is a graph of tumor growth versus time in MM1S xenograft tumor-bearing SCID mice treated with Compound 1 or vehicle.

As shown in FIG. 13, Compound 1 single agent inhibited tumor growth in the MM1S subcutaneous tumor model. The T/C values are calculated to be 27.37% (p<0.0001, ANOVA) based on day 14. No body weight loss or other side effects were observed for the Compound 1 single agent treatment group.

MM1R Xenograft Model

Female SCID/Beige mice at age 4 weeks were housed in ventilated micro-isolator cages (INNOCAGE®IVC, Innovive Inc., San Diego, Calif.) in a controlled climate, fed with sterile high-fat diet (Problab-RMH 2000) ad libitum and provided with sterilized water. All housing and supplies for SCID/Beige mice were sterilized by autoclaving before use. Mice were inspected daily including weekends/holidays by trained animal facility personnel and investigators. All animal procedures were performed under sterile conditions within a biosafety cabinet (for injections) or laminar flow hood (for animal husbandry and non-invasive procedures).

MM1R human MM cells were originally obtained from peripheral blood of a multiple myeloma patient (Goldman-Leiken R E, et al., *J Lab Clin Invest*. 1980, 113:335-345). Cryopreserved cells were thawed in a 37° C. water bath and cultured in RPMI medium plus 10% Fetal Bovine Serum (FBS) in a tissue culture incubator at 5% $CO_2$. Cells were sent to outside vendors for contaminants and rodent pathogen screening intended to rule out contamination by mycoplasma (by PCR) and/or virus (by MAP test, Mouse Antibody Production). When the cells in culture were enough for implantation, they washed with serum free Hank's balanced salt solution (HBSS). Finally the cells were diluted in HBSS for implantation. Only single-cell suspensions of greater than 90% viability (by trypan blue exclusion) were used for injection and 15 million cells per animal suspended in 0.1 ml HBSS were injected subcutaneously in the right hind flank region of the mouse after a minimum 7 day acclimation period, using a 1 CC syringe with a 26 G hypodermic needle, taking care to avoid blood vessels. Successful implantation was indicated by the formation of a round, raised mass under the skin. The implanted mice were monitored for general health and tumor development daily.

Tumors were detectable about two weeks following implantation. Tumor size was measured with a caliper. The following formula was used to calculate the tumor volume:

Tumor volume=(length×width$^2$)/2

Three weeks after tumor implantation, tumor reached an average of 131.7±28.7 mm$^3$. Animals with acceptable tumor size and shape were randomly assigned into two groups of eight animals each, using sorting software, one vehicle control and one treatment group.

Compound 1 was formulated and dosed as follows: 7.5 mg/ml was dissolved in 30% Captisol with 2 molar equivalents of NaOH and HCl each and dosed by oral gavage everyday five times per week based on body weight of each mouse. The control group was dosed with vehicle (30% Captisol) using same dosing paradigm.

During each animal study, tumors were measured with calipers, tumor size determined using the above mentioned formula, and tumor size changes in percentage calculated. Mouse body weights were measured with a scale twice per week. Studies were continued until either: a) the predetermined end date indicated in the study design; or b) the onset of health problems, whichever occurred first. In addition, the following tumor-related parameters warranted provision of euthanasia: (1) tumor burden exceeding 2500 mm$^3$ and/or (2) loss of ≥20% of starting body weight. In addition to the determination of tumor size changes, the last tumor measurement was used to generate the tumor weight change ratio (T/C value), a standard metric developed by the National Cancer Institute (NCI) for xenograft tumor evaluation. T/C values were calculated using the following formula: % T/C=100× $\Delta T/\Delta C$ if $\Delta T>0$. In cases where tumor regression occurred, however, the following formula was used: % $T/T_0=100\times\Delta T/T0$ if $\Delta T<0$.

The treatment period was 18 days. Tumor sizes and body weights were measured again on the last day of the study.

Figure 14:
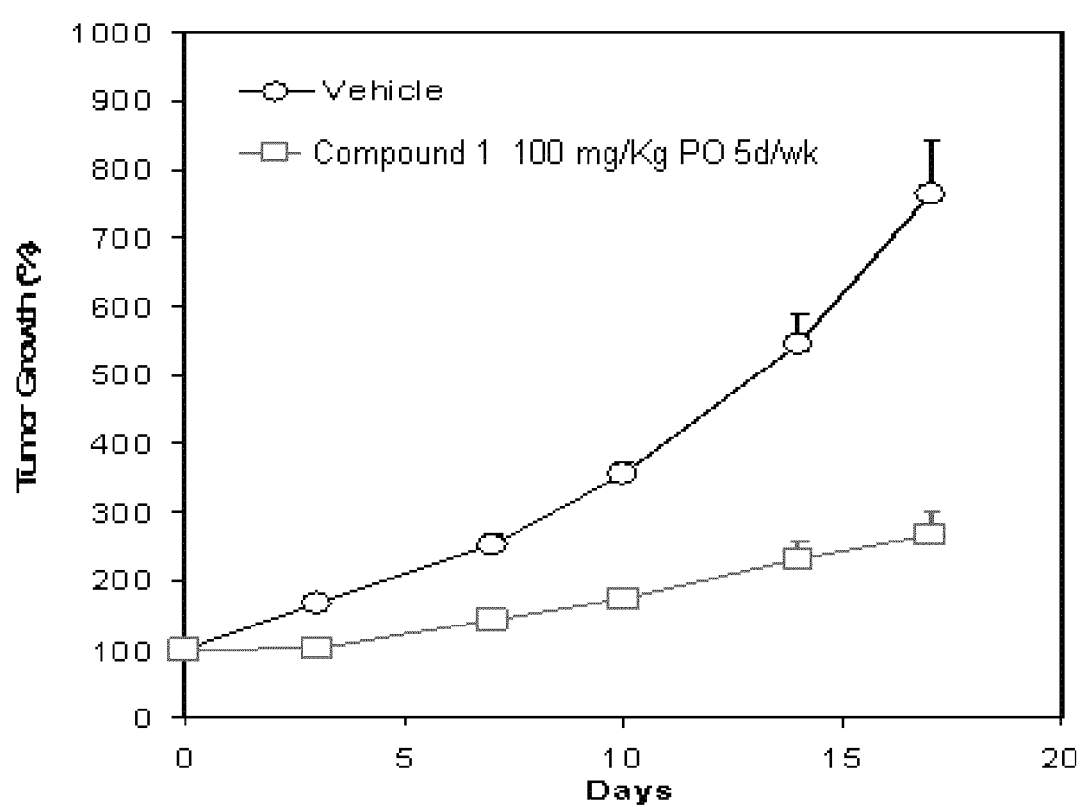
FIG. 14 is a graph of tumor growth versus time in MM1R xenograft tumor-bearing SCID mice treated with Compound 1 or vehicle.

As shown in FIG. 14, Compound 1 single agent inhibited tumor growth in the MM1R subcutaneous tumor model. The T/C values are calculated to be 21.15% (p<0.0001, ANOVA) based on day-17. No body weight loss or other side effects were observed for the Compound 1 single agent treatment group.

Example 15

Effect of Compound 1 on Circulating Lymphocytes

A study examining the effect of Compound 1 on circulating T and B lymphocytes was conducted in CD1 wild type mice. Five mice were treated with Compound 1 formulated as in Example 8(b) (5 mg/mL) at 100 mg/kg orally for five consecutive days. Another 5 mice were treated with vehicle. Blood was collected at various time points (including pre-dosing, during dosing and post-dosing) from the mandibular vein. Blood was analyzed with a flow cytometer for T and B cell quantification.

The effect of Compound 1 on T and B lymphocyte levels in lymphoid organs, spleen and lymph nodes, was also evaluated. Mice were treated with Compound 1 orally at 100 mg/kg for five consecutive days. The animals were sacrificed, and the lymphoid organs were collected. Cells were physically dissociated from the tissues and analyzed with a flow cytometer. Anti-CD3 and -CD 19 antibodies were used to stain T and B cells, respectively.

Figure 6:
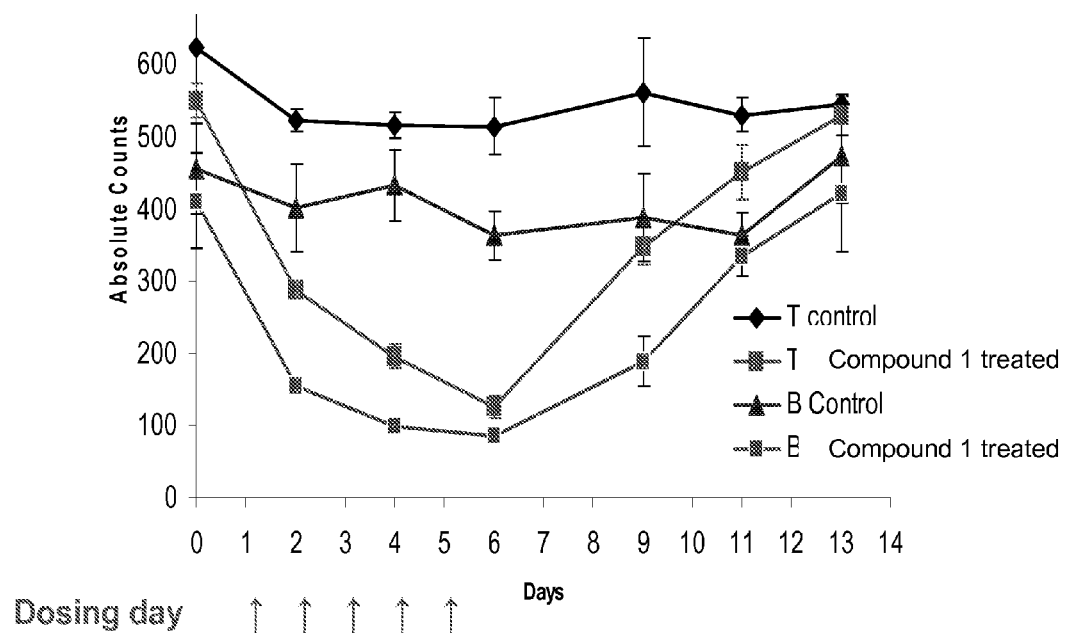
FIG. 6 is a graph showing circulating blood levels of T and B lymphocytes following treatment with Compound 1 or vehicle.

The results of these studies are shown in FIG. 6, a graph showing blood lymphocyte levels over time. Compound 1 shows a significant reversible reduction in the blood levels of both T and B lymphocytes compared to control. A similar effect is seen in lymphocyte levels in the spleen and lymph nodes. Both of these organs show a significant reduction in both T and B lymphocytes following dosing with Compound 1 compared to controls.

Example 16

Effect of Compound 1 on Hematopoietic Cells in Bone Marrow

Bone marrow was also removed from the mice sacrificed in Example 12. Bone marrow content were collected from the mice long bones and analyzed with flow cytometer. Various markers for progenitor or mature lymphocytes were used. The results showed that treatment with Compound 1, while causing a decrease in peripheral T and B lymphocyte counts, induced a compensatory increase in marrow lymphocyte progenitor cells compared to controls.

Example 17

Mini-Salmonella/Mammalian-Microsome Reverse Mutation Assay

This study was conducted to evaluate the ability of Compound 1 to induce reverse mutations either in the presence or absence of mammalian microsomal enzyme (S9-mix) at the histidine locus in the genome of 2 strains of *Salmonella typhimurium* (TA98 and TA100).

The tester strains used in the mutagenicity assay were *Salmonella typhimurium* tester strains TA98 (for detecting frame-shift reverse mutation) and TA100 (for detecting point reverse mutation). The assay was conducted in both the presence and absence of S9 mixture along with concurrent vehicle (DMSO, 20 µl/well) and positive controls in duplicate using E-well plates. Five concentrations with 2× succeeding dilutions ranging from 1000 to 62.5 µg/well (equivalent to 5000 to 312.5 µg/plate in standard Ames assay) were tested for each of the compounds. After incubation at 37° C. for 48-72 hours, plates were observed for compound insolubility and cytotoxicity, and scanned to count revertants colonies. A reproducible two-fold increase (>2× of vehicle control) of revertant colonies over the daily average control value is considered a positive response of gene mutation for each strain.

Compound 1 was dissolved in dimethyl sulfoxide (DMSO), which also served as the negative (vehicle) control. 2-nitrofluorene and sodium azide served as the positive controls in the absence of S9 for TA98 and TA100 respectively.

2-Aminoanthracene served as the positive controls in the presence of S9 for TA98 and TA100.

Results

Compound 1 formed a maroon solution when dissolved in DMSO at a concentration of 50 mg/ml, which was the most concentrated stock solution. The test article remained a light maroon to colorless solution in all 2× succeeding dilutions down to 3.125 mg/ml. The precipitation of the test article was observed when the test article and soft agar were mixed together at the concentration of 250 m/well and above. After 48-72 hours incubation, test article precipitation was seen slightly under dissecting microscopy at 250 μg/well with TA98 and TA100 in the absence of S9 mix only, test article precipitation and minor reduction of background lawn were seen slightly to moderately at 500 and 1000 μg/well with TA98 and TA100 in the presence and absence of S9 mix. There was no evidence of a significant increase in the mean number of revertant colonies compared to the average control when tested in the presence and absence of S9 mix with strains TA98 and TA100 (Table 5).

Results from the current study showed that Compound 1 did not induce a positive mutagenic response with strains TA98 and TA100 in presence and absence of microsomal enzymes when the test articles were tested up to the maximum concentration of 1000 μg/well (equivalent to 5000 μg/plate in standard Ames assay).

tured and treated with DMSO alone (vehicle control) or 0.1 μmol/L Compound 1 or reference compound for 16 hours. Cell extracts were prepared in the presence of SDS and 2-mercaptoethanol and resolved in polyacrylamide gels. Proteins were transferred to nitrocellulose filter and blotting was done using standard procedures with blocking solutions (Li-Cor Bioscience) containing the indicated primary antibody. Primary antibodies against p-EGFR, EGFR, p-HER2, HER2, p-HER3, HER3, p-MET, MET, p-bRaf, p-cRaf, pMEK, MEK, p-ERK, ERK and tubulin were purchased from Cell Signaling Technology. Secondary antibody conjugated with IRdye 680, 800CW were used and the signal was detected with Li-Cor Odyssey Imager.

Immunocytochemistry was performed on cells grown in monolayer culture that were treated as indicated in the figure legends and then fixed in 4% (w/v) paraformaldehyde. After washing in 1×PBS, immunostaining was performed in Li-Cor blocking solution containing the indicated primary antibodies and IRDye 680- or 800CW-conjugated secondary antibodies. For in-cell-western, a Li-Cor Odyssey infrared imager was used for detection and quantification of results.

For histological examination of pharmacodynamic markers, tumor xenografts were harvested and embedded in paraffin, and then 4-5-mm sections were prepared. The sections were mounted on slides and reacted with primary antibodies followed by horseradish peroxidase-conjugated secondary

TABLE 5

Mutagenicity Assay Results of Compound 1
REVERTANTS PER WELL

| | Conc. | TA98 | | | TA100 | | | Background Lawn[c] TA98/ |
|---|---|---|---|---|---|---|---|---|
| | μg/well | 1 | 2 | Mean | 1 | 2 | Mean | TA100 |
| MICROSOMES: NONE (−S9) | | | | | | | | |
| DMSO | — | 5 | 6 | 6 | 26 | 32 | 29 | 4/4 |
| Compound 1 | 62.5 | 4 | 4 | 4 | 34 | 30 | 32 | 4/4 |
| Compound 1 | 125 | 4 | 6 | 5 | 32 | 34 | 33 | 4/4 |
| Compound 1 | 250 | 6 | 5 | 6 | 34 | 29 | 32 | 4,sp/4,sp |
| Compound 1 | 500 | 5 | 3 | 4 | 33 | 31 | 32 | 3,sp/3,sp |
| Compound 1 | 1000 | 4 | 5 | 5 | 28 | 26 | 27 | 3,mp/3,mp |
| POSITIVE CONTROL[a] | | 55 | 63 | 59* | >300 | >300 | >300* | 4/4 |
| MICROSOMES (+S9) | | | | | | | | |
| DMSO | — | 6 | 6 | 6 | 34 | 33 | 34 | 4/4 |
| Compound 1 | 62.5 | 4 | 6 | 5 | 34 | 30 | 32 | 4/4 |
| Compound 1 | 125 | 6 | 3 | 5 | 28 | 30 | 29 | 4/4 |
| Compound 1 | 250 | 8 | 6 | 7 | 30 | 28 | 29 | 4/4 |
| Compound 1 | 500 | 6 | 6 | 6 | 32 | 37 | 35 | 3,sp/3,sp |
| Compound 1 | 1000 | 6 | 7 | 7 | 33 | 34 | 34 | 3,mp/3,mp |
| POSITIVE CONTROL[b] | | >300 | >300 | >300* | >300 | >300 | >300* | 4/4 |

[a]TA98: 2-nitrofluorene, 0.4 μg/well; TA100: Sodium azide, 2.0 μg/well
[b]TA98 and TA100: 2-aminoanthracene, 0.8 μg/well
[c]Background Lawn Evaluation Codes: 5. enhanced growth compared to the solvent controls, 4. similar as vehicle control (normal, no toxicity), 3. less than 25% reduction (less than 25% cytotoxicity), 2. more than 25% but less than 50% reduction (less than 50% cytotoxicity), 1. more than 50% reduction (more than 50% cytotoxicity), 0. no growth (100% cytotoxicity).
sp = slight precipitate
mp = moderate precipitate
hp = heavy precipitate
*positive increase Example 18

Pharmacodynamic Study in Tumor Cell Lines

Tumor cell lines H460 (Kras, PI3K), BT474 (HER2, PI3K), A375 (B-Raf) and H1975 (EGFR, PI3K) were cultured antibody (Envision polymer-HRP, Dako, Glostrup, Denmark). The color reaction was then performed using diaminobenzidine (DAB) as recommended by the supplier. Counterstaining of the sections was done with hematoxylin.

Figure 7:
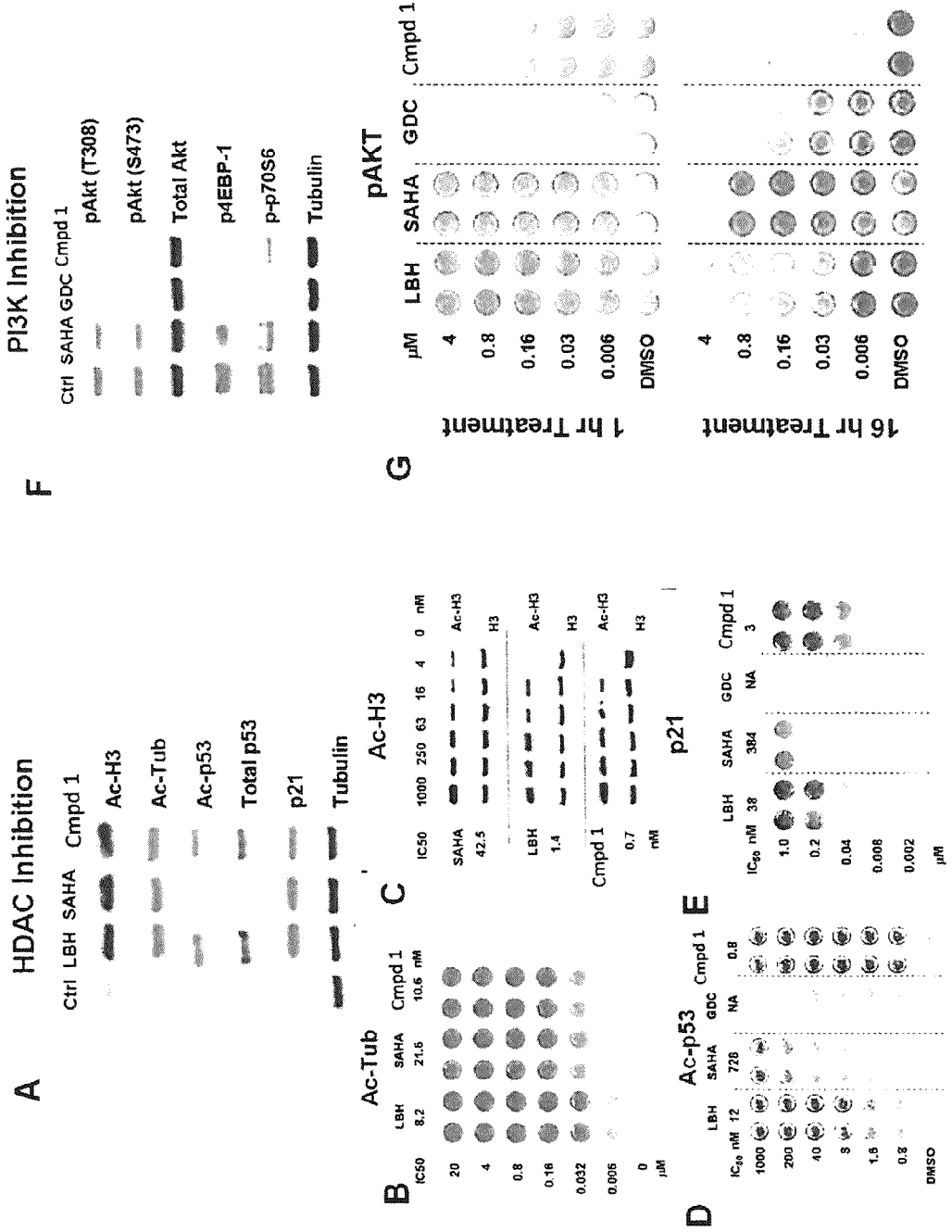
FIGS. 7A to 7G present Western blots of extracts from control and Compound 1 treated H460 (Kras, PI3K) cells. GDC is GDC-0941; LBH is LBH-589.

The results of this study are summarized in FIGS. 7A-7g and 8A-8C. Compound 1 inhibits HDAC activity and PI3K pathway signaling in KRAS- and PI3KCA-mutant H460 non-small cell lung cancer (NSCLC) cells. Cells were treated with DMSO alone (vehicle control) or containing test compounds for 1 h before Western blot or in-cell-western was performed. FIG. 7A shows that Compound 1 at 1 μmol/L increases the levels of acetylated histone 3 (Ac-H3), tubulin (Ac-Tub), and p53 (Ac-p53). The compound also upregulates total p53 and p21 content. The data set forth in FIGS. 7B-7E show that Compound 1 increases levels of acetylated-tubulin (FIG. 7B), acetylated histone 3 (FIG. 7C), acetylated p53 (FIG. 7D), and acetylated p21 (FIG. 7E) in a dose-dependent manner. Resulting $IC_{50}$ values suggest that Compound 1 has comparable HDAC-inhibitory potency to LBH 589 in the cancer cells examined. At 1 μmol/L, Compound 1 inhibits the activation of AKT and the downstream signaling proteins 4EBP-1 and p70S6 (FIG. 7F). Compound 1 also persistently and potently inhibits phosphorylation of Akt in a dose-dependent manner (FIG. 7G).

One major limitation of PI3K inhibitors in the treatment of cancers is the activation of the RAF-MEK-ERK pathway. HDAC inhibitors are able to inhibit kinase levels in this signaling pathway in cancer cells via epigenetic modification. In tumors cells with various mutations, such as the KRAS and PI3K mutations in H460 cells, the B-Raf mutation in A375 cells, HER2 and PI3K mutations in BT-474 cells, and EGFR mutations in H1975 cells, 100 nM Compound 1 suppressed activation of Raf, MEK, and ERK. The potent HDAC inhibitor LBH 589 showed similar activities in some of these Western blot assays (FIG. 8A).

Figure 8:
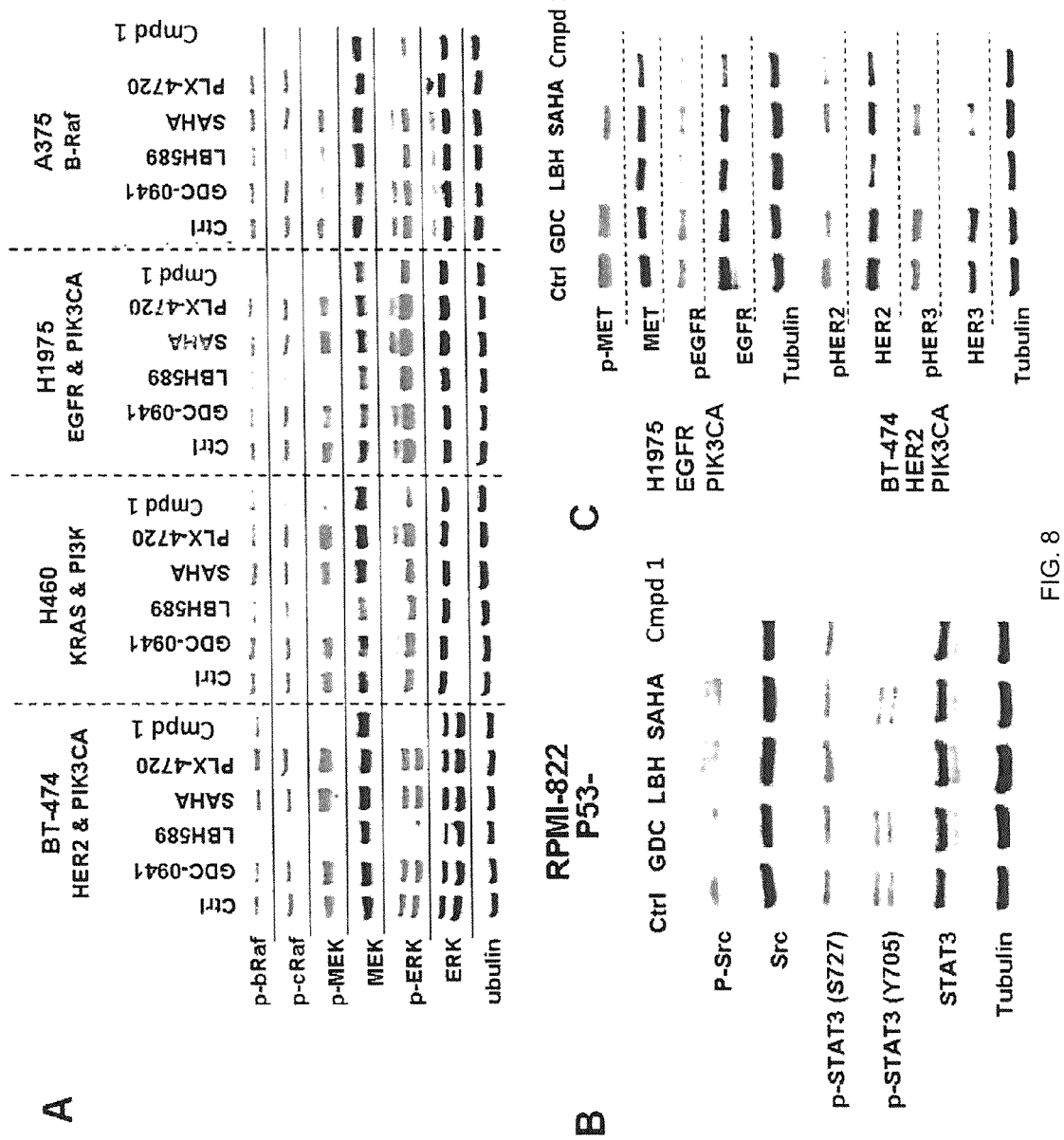
FIGS. 8A to 8C present Western blots of extracts from control and Compound 1 treated H1975 (EGFR, PI3K), BT474 (HER2, PI3K), H1975 (EGFR, PI3K), A375 (B-Raf) and RPMI-822 (p53⁻) cells.
Figure 9:
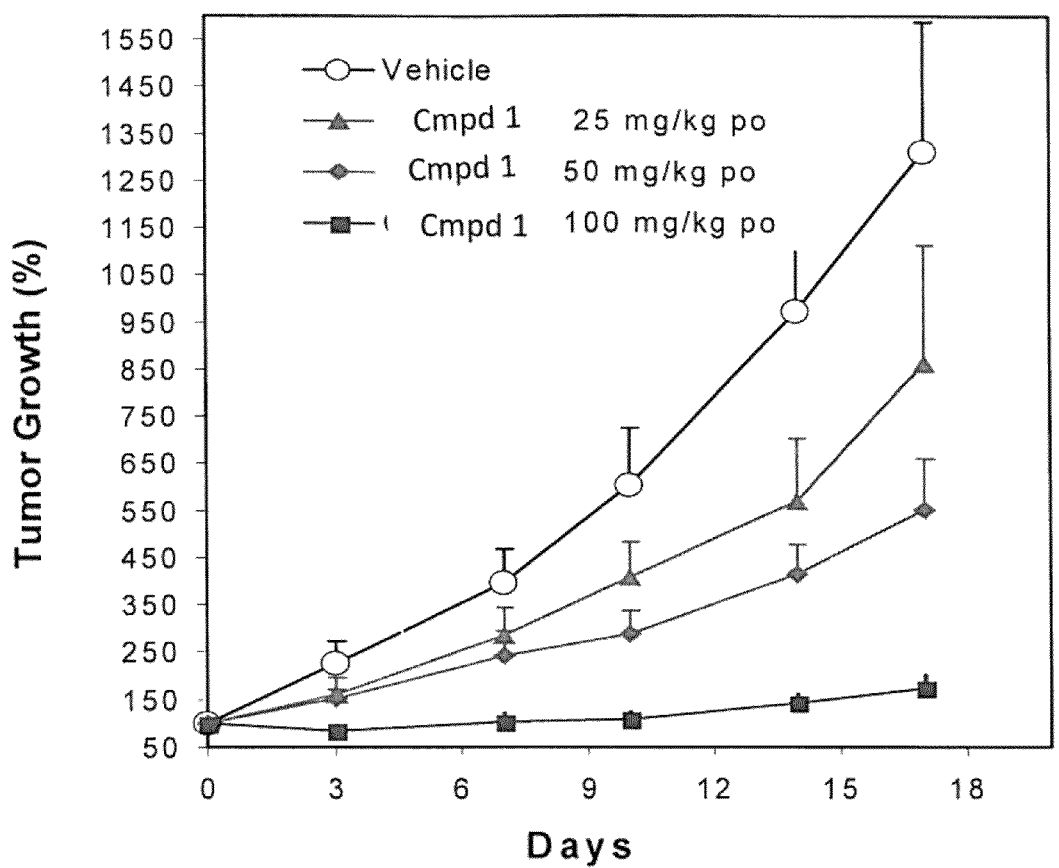
FIG. 9 is a graph of tumor growth versus time in Daudi xenograft tumor-bearing Scid mice treated orally with Compound 1 or vehicle.

In addition to inhibition of the PI3K and MEK pathways, treatment of RPMI-8226 myeloma cells with 1 μM Compound 1 for 16 h inhibited p-STAT3 (Y-705) and p-Src (FIG. 8B).

In EGFR-L858R-T790M double-mutant H1975 NSCLC cells and HER2-overexpressing BT-474 breast cancer cells, Compound 1 was shown to reduce the levels of phosphorylated and total receptor tyrosine kinases EGFR, HER2, HER3, and MET after incubation for 16 h. Similar downregulation of the same kinases was observed after treatment of these cells with LBH 589 (FIG. 8C).

Example 19

Expression of PI3K110 α, β, γ and δ in Hematological Xenograft Tumor Models

Female immuno-deficient mice (Beige/SCID) at age 6-8 weeks were housed in ventilated micro-isolator cages in a controlled climate, fed with sterile high-fat diet (Problab-RMH 2000) ad libitum and provided sterilized water. All housing and supplies for SCID beige mice were disposable, and purchased irradiated from Innovive prior to use. Mice were inspected daily including weekends/holidays by trained animal facility personnel and investigators. All animal procedures were performed under sterile conditions within a biosafety cabinet (for injections) or laminar flow hood (for animal husbandry and non-invasive procedures).

Human hematological cancer cell lines were originally obtained from human cancer patients. Cryopreserved cells were thawed in a 37° C. water bath and cultured in RPMI medium plus 10-15% Fetal Bovine Serum (FBS) in a tissue culture incubator at 5% $CO_2$. Cells were sent to outside vendors for contaminants and rodent pathogen screening intended to rule out contamination by mycoplasma (by PCR) and/or virus (by MAP test, Mouse Antibody Production).

When the cells in culture reached desired number, they were harvested and washed with serum free Dulbecco's phosphate buffered saline (DPBS). Finally the cells were diluted in DPBS for implantation. Only single-cell suspensions of greater than 90% viability (by trypan blue exclusion) were used for injection. After a seven day acclimation period, 10 to 20 million cells per animal suspended in 0.1 ml DPBS were injected subcutaneously (SC) in the right hind flank region of the animal using a 0.5 CC syringe with a 26 G hypodermic needle, taking care to avoid blood vessels. Successful implantation was indicated by the formation of a round, raised mass under the skin. The implanted mice were monitored for general health and tumor development daily.

Tumors were detectable about two and half weeks following implantation. Tumor size was measured with a caliper. The following formula was used to calculate the tumor volume:

$$\text{Tumor volume} = (\text{length} \times \text{width}^2)/2$$

When tumor sizes reached about 150-300 mm³, mice were separated into four groups including three treatment groups (25 mg/kg, 50 mg/kg and 100 mg/kg) and one control group. Following dosing with Compound 1, tumors were collected at 15 minutes, 1, 3, 6, 24 hours (3 mice for each time point). Tumors were collected according to the time points listed above after mice were euthanized with $CO_2$. Samples were placed in the dry ice until transferred to a −80° C. freezer for Western blot analysis.

Protein was extracted from the tumor tissues using a homogenizer (Tissuelyser, Qiagen, Valencia, Calif.) according to the manufacturer's instructions. The adapters for holding the tissue tubes were frozen at −20° C., and the lysis buffer and beads were chilled at 4° C. before use.

100-200 μg tissue was homogenized in 300 μl T-PER Mammalian Tissue Protein Extraction reagent (Pierce, Rockford, Ill.) supplemented with phosphatase inhibitors (1:100 v/v, Tyr & Ser/Thr phosphatase inhibitor cocktails, Upstate). The specimen were checked visually after each cycle (time: 0.15 minutes; frequency: 30 Hz) until tissues were fully homogenized. Approximately four cycles were needed in most cases. The tissue lysates were centrifuged at 14,000 rpm at 4° C. for 10 minutes. 200 μl supernatant was collected and kept at −80° C. Protein concentration was measured using the BCA Protein Assay kit (Pierce, Rockford, Ill.) according to the manufacturer's instructions.

30 μg of total protein extract was resolved on NuPAGE Novex 4-12% Bis-Tris gels (Invitrogen) and transferred to nitrocellulose membranes (Bio-Rad) using a Bio-Rad Semi-Dry Transfer Machine. The blots were incubated with 10 ml Blocking Buffer (Odyssey Infrared Imaging System) for 1 hour and then probed with the primary antibody overnight at 4° C. on a shaker. The blots were probed with the primary antibody overnight at 4° C. Primary antibodies included PI3 Kinase p110α (#4249, 1:1000, Cell Signaling), PI3 Kinase p110β (#3011, 1:1000, Cell Signaling), PI3 Kinase p110γ (#5405, 1:1000, Cell Signaling), PI3 Kinase p110δ (SC-7176 (1:1000, Santa Cruz Biotechnology, Santa Cruz, Calif.). GAPDH (glyceraldehyde 3-phosphate dehydrogenase, 1/30, 000, Abcam, Cambridge, Mass.) was used as an internal control for each assay.

The membrane was rinsed four times with Tris-buffered saline Tween-20 (TBST; DAKO) and incubated for 1 hour at room temperature with the infrared conjugated secondary antibodies (1:10000): anti-Rabbit conjugated-IR Dye 800 (Rockland), or anti-Mouse conjugated-Alexa 680 (Molecular Probes). The membrane was washed with TBST and then placed in the Odyssey Infrared Imaging System for imaging and analysis.

Figure 15:
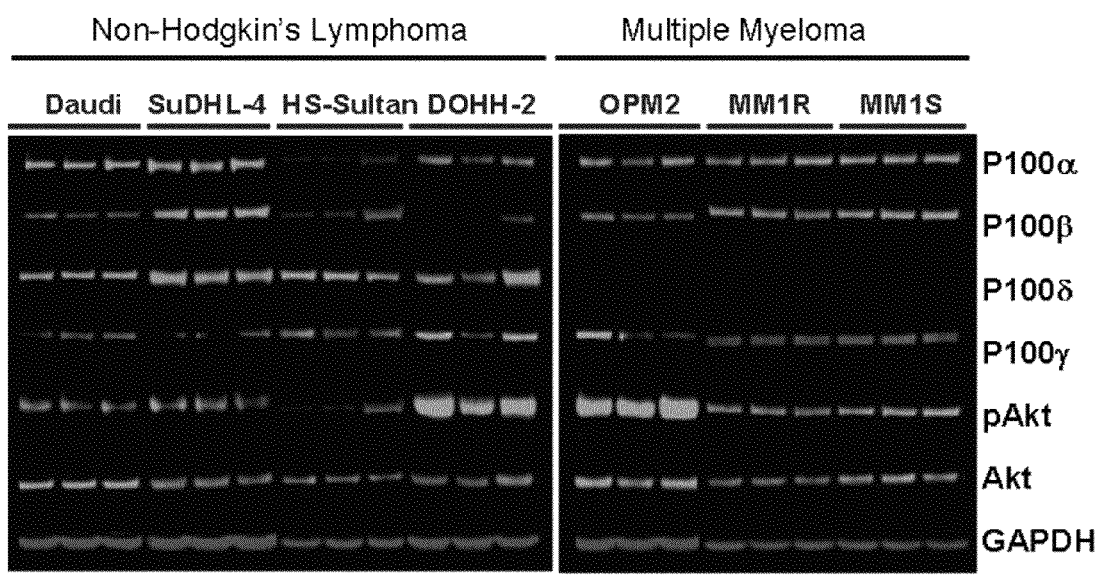
FIG. 15 presents Western blots of tumor extracts from Compound 1 treated SCID mice bearing Daudi, SuDHL-4, HS-Sultan, DOHH-2, OPM-2, MM1R or MM1S xenograft tumors.

The results are set forth in FIG. 15, which shows Western blots of PI3K p110 isoforms, AKT and pAKT from several Non-Hodgkin's Lymphoma and multiple myeloma xenografts. The results show that activation of AKT is driven by multiple PI3K P110 isoforms.

Example 20

Comparison of Compound 1 and CAL-101 in the Daudi Xenograft Tumor Model

Female SCID beige mice (CD-1 Beige SCID) at 6-8 weeks of age were housed in ventilated micro-isolator cages in a controlled climate, fed with sterile high-fat diet (Problab-RMH 2000 ad libitum and provided with sterilized water. All housing and supplies for SCID beige mice are disposable, and purchased irradiated from Innovive prior to use. Mice were inspected daily including weekends/holidays by trained animal facility personnel and investigators. All animal procedures were performed under sterile conditions in a biosafety cabinet (for injections) or laminar flow hood (for animal husbandry and non-invasive procedures).

Daudi human Burkitt's lymphoma cells were originally obtained from a human Burkitt's lymphoma patient. Cryopreserved cells were thawed in a 37° C. water bath and cultured in RPMI-1640 medium plus 15% Fetal Bovine Serum (FBS), 1% Penstrep, and 1% Glutamax in a tissue culture incubator at 5% $CO_2$. Cells were sent to outside vendors for pathogen screening intended to rule out contamination by mycoplasma (by PCR) and/or virus (by MAP test, Mouse Antibody Production). When the cells in culture reached desired numbers, they were harvested by centrifuging. After collection, the cells were washed with serum-free Dulbecco's phosphate buffered saline (DPBS). Finally the cells were diluted in DPBS for implantation. Only single-cell suspensions of greater than 90% viability (by trypan blue exclusion) were used for injection and 20 million cells per animal suspended in 0.1 ml DPBS were injected subcutaneously in the right hind flank region of the mouse after a minimum 7 day acclimation period, using a 0.5 CC syringe with a 26 G hypodermic needle, taking care to avoid blood vessels. Successful implantation was indicated by the formation of a round, raised mass under the skin. The implanted mice were monitored for general health and tumor development daily.

Tumors were detectable about two weeks following implantation. Tumor size was measured with a caliper. The following formula was used to calculate the tumor volume:

Tumor volume=(length×width$^2$)/2

Four weeks after tumor implantation, tumors reached an average size of 300±126 mm$^3$. Animals with acceptable tumor size and shape were randomly assigned into three groups of seven animals each, using sorting software, one vehicle control and two treatment groups.

| Groups | Number of mice | Compounds | Dose (mg/kg) | Schedule |
|---|---|---|---|---|
| 1 | 7 | 30% Captisol | 0 | Qd* (Mon-Fri), PO** |
| 2 | 7 | CAL-101 | 30 | BID*** (Mon-Fri) |
| 3 | 7 | Compound 1 | 100 | Qd* (Mon-Fri), PO** |

*Qd = Once daily dosing,
**PO = Oral Gavage dosing,
***BID, twice daily

Compound 1 was formulated and dosed as follows: Compound 1 (7.5 mg/ml) was dissolved in 30% Captisol with 2 molar equivalents of NaOH, balanced with 2 molar equivalents of HCl, and dosed via oral gavage daily Monday through Friday. The control group was dosed with vehicle (30% Captisol) using the same dosing paradigm as the 100 mg/kg volume (6.67 ul/g).

During each animal study, tumors were measured with calipers, tumor size determined using the above mentioned formula, and tumor size changes in percentage calculated. Mouse body weights were measured with a scale twice per week. Studies were continued until either: a) the predetermined end date indicated in the study design; or b) the onset of health problems, whichever occurred first. In addition, the following tumor-related parameters warranted provision of euthanasia: tumor burden exceeding 2500 mm$^3$ and/or loss of 20% of starting body weight. In addition to the determination of tumor size changes, the last tumor measurement was used to generate the tumor weight change ratio (T/C value), a standard metric developed by the National Cancer Institute (NCI) for xenograft tumor evaluation. T/C values were calculated using the following formula: % T/C=100×ΔT/ΔC if ΔT>0. In cases where tumor regression occurred, however, the following formula was used: % T/T$_0$=100×ΔT/T0 if ΔT<0.

The treatment period was 15 days for the vehicle and CAL-101 groups, which required earlier termination due to tumor size exceeding 10% of body weight, and 18 days for the Compound 1 group. Tumor sizes and body weights were measured again on the last day of the study.

Figure 16:
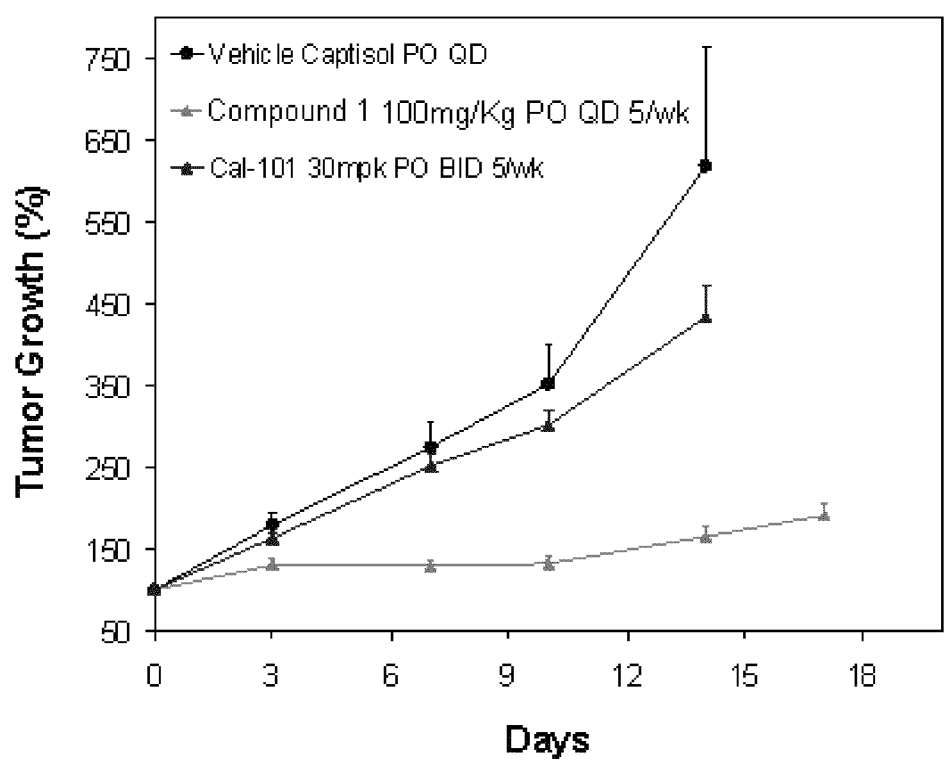
FIG. 16 is a graph of tumor growth versus time in Daudi tumor-bearing SCID mice treated with Compound 1, CAL-101 or vehicle.

The results of the study are presented in FIG. 16, which shows tumor growth for the active and control groups as a function of treatment time. The Compound 1 group showed significantly reduced tumor growth compared to the CAL-101 and control groups.

Example 21

Combination of Compound 1 and Cyclophosphamide in the Daudi Xenograft Tumor Model Female SCID beige mice (CD-1 Beige SCID) at 6-8 weeks of age were housed in ventilated micro-isolator cages in a controlled climate, fed with sterile high-fat diet (Problab-RMH 2000 ad libitum and provided with sterilized water. All housing and supplies for SCID beige mice are disposable, and purchased irradiated from Innovive prior to use. Mice were inspected daily including weekends/holidays by trained animal facility personnel and investigators. All animal procedures were performed under sterile conditions in a biosafety cabinet (for injections) or laminar flow hood (for animal husbandry and non-invasive procedures).

Daudi human Burkitt's lymphoma cells were originally obtained from a human Burkitt's lymphoma patient. Cryopreserved cells were thawed in a 37° C. water bath and cultured in RPMI-1640 medium plus 15% Fetal Bovine Serum (FBS), 1% Penstrep, and 1% Glutamax in a tissue culture incubator at 5% $CO_2$. Cells were sent to outside vendors for pathogen screening intended to rule out contamination by mycoplasma (by PCR) and/or virus (by MAP test, Mouse Antibody Production). When the cells in culture reached desired numbers, they were harvested by centrifuging. After collection, the cells were washed with serum-free Dulbecco's phosphate buffered saline (DPBS). Finally, the cells were diluted in DPBS for implantation. Only single-cell suspensions of greater than 90% viability (by trypan blue exclusion) were used for injection and 20 million cells per animal suspended in 0.1 ml DPBS were injected subcutaneously into the right hind flank region of the mouse after a minimum 7 day acclimation period, using a 0.5 cc syringe with a 26 G hypodermic needle, taking care to avoid blood vessels. Successful implantation was indicated by the formation of a round, raised mass under the skin. The implanted mice were monitored for general health and tumor development daily.

Tumors were detectable about two weeks following implantation. Tumor size was measured with a caliper. The following formula was used to calculate the tumor volume:

Tumor volume=(length×width$^2$)/2

Four weeks after tumor implantation, tumors reached an average size of 189±47 mm$^3$. Animals with acceptable tumor size and shape were randomly assigned into four groups of eight animals each, using sorting software, one vehicle control and three treatment groups.

| Groups | Number of mice | Compounds | Dose (mg/kg) | Schedule |
|---|---|---|---|---|
| 1 | 8 | 30% Captisol 0.9% NS | 0 | Qd* (Mon-Fri), PO** |
| 2 | 8 | Compound 1 | 75 | Qd* (Mon-Fri), PO** |
| 3 | 8 | CTX | 50 | Day-0, iv |
| 4 | 8 | Compound 1 + CTX | 75 50 | Qd* (Mon-Fri), PO** Day-0, iv |

*Qd = Once daily dosing,
**PO = Oral Gavage dosing,
***BID, twice daily

Compound 1 was formulated and dosed as follows: Compound 1 (7.5 mg/ml) was dissolved in 30% Captisol with 2 molar equivalents of NaOH, balanced with 2 molar equivalents of HCl, and dosed via oral gavage daily Monday through Friday at 75 mg/kg. Cyclophosphamide ("CTX") was dissolved in 0.9% NS at 5 mg/ml, and dosed iv (tail vein injection) to animals at 50 mg/kg on Day-0. The combination group was dosed with both Compound 1 and CTX using same dosing schedule. The control group was dosed with vehicle (30% Captisol) and 0.9% NS using the same paradigm as for the combination.

During each animal study, tumors were measured with calipers, tumor size determined using the above mentioned formula, and tumor size changes in percentage calculated. Mouse body weights were measured with a scale twice per week. Studies were continued until either: a) the predetermined end date indicated in the study design; or b) the onset of health problems, whichever occurred first. In addition, the following tumor-related parameters warranted provision of euthanasia: tumor burden exceeding 2500 mm$^3$ and/or loss of 20% of starting body weight. In addition to the determination of tumor size changes, the last tumor measurement was used to generate the tumor weight change ratio (T/C value), a standard metric developed by the National Cancer Institute (NCI) for xenograft tumor evaluation. T/C values were calculated using the following formula: % T/C=100×ΔT/ΔC if ΔT>0. In cases where tumor regression occurred, however, the following formula was used: % T/T$_0$=100×ΔT/T0 if ΔT<0.

The treatment period was 2 weeks. Tumor sizes and body weights were measured again on the last day of the study.

Figure 17:
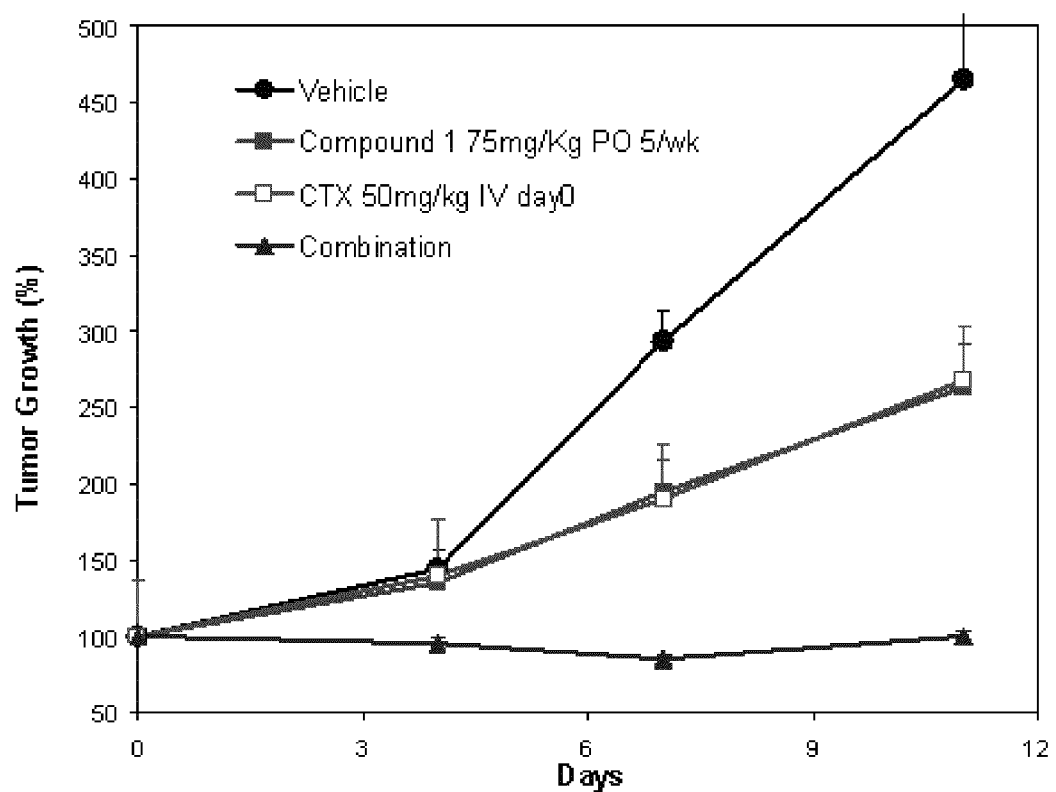
FIG. 17 is a graph of tumor growth versus time in Daudi tumor-bearing SCID mice treated with Compound 1, cyclophosphamide, combination of Compound 1 and cyclophosphamide or vehicle.

The results of this study are set forth in FIG. 17, which shows tumor growth as a function of treatment time for the control and treatment groups. As single agents, Compound 1 and cyclophosphamide have similar activity in this model. The combination of Compound 1 and cyclophosphamide showed substantially greater efficacy than either agent alone.

Example 22

Compound 1 in Combination with Lenalidomide in the MM1S Xenograft

Model

Female SCID/Beige mice at age 4 weeks were housed in ventilated micro-isolator cages (INNOCAGE®IVC, Innovive Inc., San Diego, Calif.) in a controlled climate, fed with sterile high-fat diet (Problab-RMH 2000) ad libitum and provided with sterilized water. All housing and supplies for SCID/Beige mice were sterilized by autoclaving before use. Mice were inspected daily including weekends/holidays by trained animal facility personnel and investigators. All animal procedures were performed under sterile conditions within a biosafety cabinet (for injections) or laminar flow hood (for animal husbandry and non-invasive procedures).

Cryopreserved MM1S human MM cells were thawed in a 37° C. water bath and cultured in RPMI medium plus 10% Fetal Bovine Serum (FBS) in a tissue culture incubator at 5% $CO_2$. Cells were sent to outside vendors for contaminants and rodent pathogen screening intended to rule out contamination by mycoplasma (by PCR) and/or virus (by MAP test, Mouse Antibody Production). When the cells in culture were enough for implantation, they washed with serum free Hank's balanced salt solution (HBSS). Finally the cells were diluted in HBSS for implantation. Only single-cell suspensions of greater than 90% viability (by trypan blue exclusion) were used for injection and 20 million cells per animal suspended in 0.2 ml HBSS were injected subcutaneously in the right hind flank region of the mouse after a minimum 7 day acclimation period, using a 1 CC syringe with a 26 G hypodermic needle, taking care to avoid blood vessels. Successful implantation was indicated by the formation of a round, raised mass under the skin. The implanted mice were monitored for general health and tumor development daily.

Tumors were detectable about two weeks following implantation. Tumor size was measured with a caliper. The following formula was used to calculate the tumor volume:

Tumor volume=(length×width$^2$)/2

Three weeks after tumor implantation, tumor reached an average of 192±32 mm$^3$. Animals with acceptable tumor size and shape were randomly assigned into 6 groups of 7 animals each, using sorting software, one vehicle control and six treatment groups.

| Groups | Number of mice | Compounds | Dose (mg/kg) | Schedule |
|---|---|---|---|---|
| 1 | 7 | 30% Captisol MCT | 0 | Qd* (Mon-Fri), PO** Qd* (Mon-Fri), PO** |
| 2 | 7 | Compound 1 | 75 | Qd* (Mon-Fri), PO** |
| 3 | 7 | Lenalidomide | 12.5 | Qd* (Mon-Fri), PO** |
| 4 | 7 | Lenalidomide | 12.5 | Qd* (Mon-Fri), PO** |
| 5 | 7 | Compound 1 + Lenalidomide | 75 12.5 | Qd* (Mon-Fri), PO** Qd* (Mon-Fri), PO** |
| 6 | 7 | Compound 1 + Lenalidomide | 75 25 | Qd* (Mon-Fri), PO** Qd* (Mon-Fri), PO** |

Compound 1 was formulated and dosed as follows: Compound 1 (7.5 mg/ml) was dissolved in 30% Captisol with 2 molar equivalents of NaOH, balanced with 2 molar equivalents of HCl, and dosed via oral gavage daily Monday through Friday at 75 mg/kg. Lenalidomide (Selleck, 2.5 mg/ml) was formulated in MCT (0.5% methyl cellulose and 0.2% Tween80), and dosed at 12.5 mg/kg or 25 mg/kg. The two combinations groups were dosed with Compound 1 at 75 mg/kg plus one dose level of lenalidomide (either 12.5 or 25 mg/kg). The control group was dosed with vehicle (30% Captisol) and MCT using the same paradigm as for the combination.

During each animal study, tumors were measured with calipers, tumor size determined using the above mentioned formula, and tumor size changes in percentage calculated. Mouse body weights were measured with a scale twice per week. Studies were continued until either: a) the predetermined end date indicated in the study design; or b) the onset of health problems, whichever occurred first. In addition, the following tumor-related parameters warranted provision of euthanasia: (1) tumor burden exceeding 2500 mm$^3$ and/or (2) loss of 20% of starting body weight. In addition to the determination of tumor size changes, the last tumor measurement was used to generate the tumor weight change ratio (T/C value), a standard metric developed by the National Cancer Institute (NCI) for xenograft tumor evaluation. T/C values were calculated using the following formula: % T/C=100× ΔT/ΔC if ΔT>0. In cases where tumor regression occurred, however, the following formula was used: % T/T$_0$=100×ΔT/ T0 if ΔT<0.

The treatment period was 17 days. Tumor sizes and body weights were measured again on the last day of the study.

Figure 18:
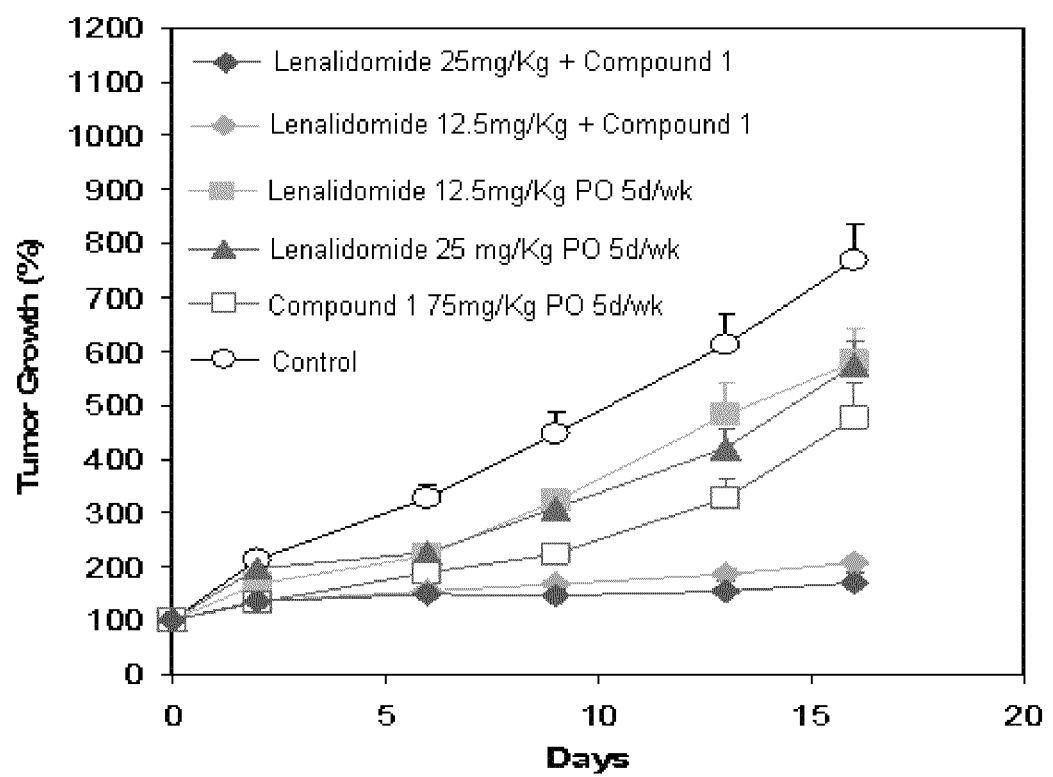
FIG. 18 is a graph of tumor growth versus time in MM1S tumor-bearing SCID mice treated with Compound 1, lenalidomide, combination of Compound 1 and lenalidomide or vehicle.

The results of this study are presented in FIG. 18, which shows tumor growth as a function of treatment time. The results show that Compound 1 at 75 mg/Kg PO is more effective than Lenalidomide at either 12.5 or 25 mg/Kg PO as single agents. The results also show that the combination of Compound 1 and lenalidomide is significantly more effective than either compound alone.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula I:

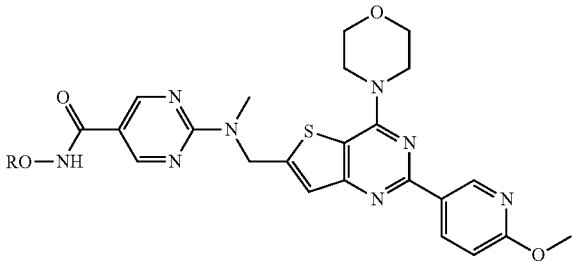 [SMILES: COc1ccc(-c2nc(N3CCOCC3)c3sc(CN(C)c4ncc(C(=O)NO)cn4)cc3n2)cn1]

or a pharmaceutically acceptable salt thereof, wherein R is hydrogen or an acyl group.

2. The compound of claim 1 wherein R is R$_1$C(O)—, wherein R$_1$ is substituted or unsubstituted C$_1$-C$_{24}$-alkyl; substituted or unsubstituted C$_2$-C$_{24}$-alkenyl; substituted or unsubstituted C$_2$-C$_{24}$-alkynyl; substituted or unsubstituted aryl; or substituted or unsubstituted heteroaryl.

3. The compound of claim 1 wherein R is H or acetyl.

4. The compound of claim 1 represented by the formula:

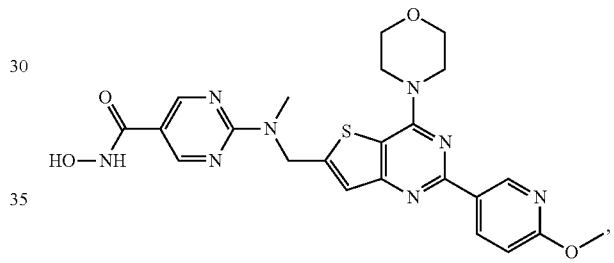

or a pharmaceutically acceptable salt thereof.

5. A pharmaceutical composition comprising as an active ingredient a compound of claim 1 and a pharmaceutically acceptable carrier.

6. A pharmaceutical composition comprising as an active ingredient a compound of claim 4 and a pharmaceutically acceptable carrier.

7. The pharmaceutical composition of claim 5 in the form of a tablet or a capsule.

8. The pharmaceutical composition of claim 6 in the form of a tablet or a capsule.

* * * * *